(12) United States Patent
Kakinuma et al.

(10) Patent No.: US 8,115,017 B2
(45) Date of Patent: Feb. 14, 2012

(54) C-PHENYL 1-THIOGLUCITOL COMPOUND

(75) Inventors: Hiroyuki Kakinuma, Toshima-ku (JP); Takahiro Oi, Toshima-ku (JP); Yohei Kobashi, Toshima-ku (JP); Yuko Hashimoto, Toshima-ku (JP); Hitomi Takahashi, Toshima-ku (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 225 days.

(21) Appl. No.: 12/305,157

(22) PCT Filed: Jun. 28, 2007

(86) PCT No.: PCT/JP2007/063031
§ 371 (c)(1),
(2), (4) Date: Dec. 16, 2008

(87) PCT Pub. No.: WO2008/001864
PCT Pub. Date: Jan. 3, 2008

(65) Prior Publication Data
US 2010/0004465 A1    Jan. 7, 2010

(30) Foreign Application Priority Data
Jun. 29, 2006 (JP) ................................. 2006-179971

(51) Int. Cl.
*C70D 335/02* (2006.01)
(52) U.S. Cl. ........................................................ 549/28
(58) Field of Classification Search ...................... 549/28
See application file for complete search history.

(56) References Cited

U.S. PATENT DOCUMENTS

| 7,169,761 B2 | 1/2007 | Tomiyama et al. |
| 2004/0176308 A1 | 9/2004 | Shiohara et al. |
| 2005/0124555 A1 | 6/2005 | Tomiyama et al. |
| 2005/0209309 A1 | 9/2005 | Sato et al. |
| 2005/0256317 A1 | 11/2005 | Sato et al. |
| 2005/0272669 A1 | 12/2005 | Fushimi et al. |
| 2006/0035844 A1 | 2/2006 | Ito et al. |
| 2007/0197623 A1 | 8/2007 | Brummerhop et al. |
| 2008/0132563 A1 | 6/2008 | Kakinuma et al. |

FOREIGN PATENT DOCUMENTS

| EP | 0 850 948 A1 | 7/1998 |
| EP | 1 270 584 A1 | 1/2003 |
| EP | 1 544 208 A1 | 6/2005 |
| WO | 01/27128 A1 | 4/2001 |
| WO | WO 01/68660 A1 | 9/2001 |
| WO | WO 02/098893 A1 | 12/2002 |
| WO | 2004/013118 A1 | 2/2004 |
| WO | 2004/014930 A1 | 2/2004 |
| WO | 2004/014931 A1 | 2/2004 |
| WO | WO 2004/014931 A1 * | 2/2004 |
| WO | WO 2004/014932 A1 | 2/2004 |
| WO | WO 2004/018491 A1 | 3/2004 |
| WO | WO 2004/019958 A1 | 3/2004 |
| WO | WO 2004/050122 A1 | 6/2004 |
| WO | WO 2005/121161 A1 | 12/2005 |
| WO | 2006/073197 A1 | 7/2006 |

OTHER PUBLICATIONS

West, Solid-State Chemistry and Its Applications, 1984, John Wiley & Sons.*

* cited by examiner

*Primary Examiner* — Nizal Chandrakumar
(74) *Attorney, Agent, or Firm* — Sughrue Mion, PLLC

(57) ABSTRACT

C-phenyl 1-thioglucitol compounds of the following formula (I) or pharmaceutically acceptable salts thereof or hydrates thereof:

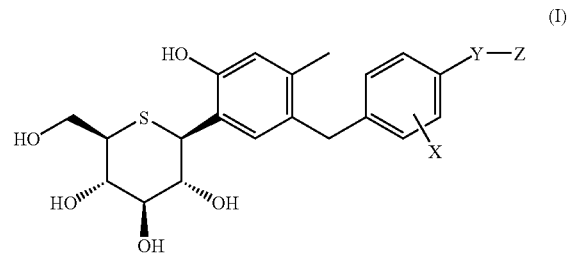

(I)

[wherein
X represents a hydrogen atom or a $C_{1-6}$ alkyl group,
Y represents a $C_{1-6}$ alkylene group or —O—$(CH_2)n$- (wherein n represents an integer of 1 to 5), and
Z represents —$CONHR^A$ or —$NHCONHR^B$ (provided that when Z represents —$NHCONHR^B$, n is not 1),
wherein
$R^A$ represents a $C_{1-6}$ alkyl group substituted with 1 to 3 substituents selected from the group consisting of a hydroxyl group and —$CONH_2$, and
$R^B$ represents a hydrogen atom or a $C_{1-6}$ alkyl group substituted with 1 to 3 substituents selected from the group consisting of a hydroxyl group and —$CONH_2$] are useful as prophylactic or therapeutic agents for diabetes, because of their suppressive effect on sugar (e.g., glucose) absorption through inhibition of SGLT1 activity, or alternatively, because of their suppressive effect on sugar (e.g., glucose) absorption and excretory effect on urinary sugars through inhibition of both SGLT1 and SGLT2 activities.

1 Claim, No Drawings ial
C-PHENYL 1-THIOGLUCITOL COMPOUND

TECHNICAL FIELD

The present invention relates to C-phenyl 1-thioglucitol compounds which have an inhibitory effect on the activity of sodium-dependent glucose transporter 1 (SGLT1) involved in absorption of glucose and other sugars in the small intestinal epithelium, or alternatively, which have not only such an inhibitory effect on SGLT1 activity but also an inhibitory effect on the activity of sodium-dependent glucose transporter 2 (SGLT2) involved in glucose reabsorption in the kidney.

BACKGROUND ART

When people suffer from diabetes, their fasting blood glucose levels reach 126 mg/dL or more. Even if fasting blood glucose levels fall within a normal range, some people exhibit postprandial blood glucose levels as high as 140 to 200 mg/dL and are diagnosed as having impaired glucose tolerance (hereinafter referred to as IGT). It has been considered that the risk of cardiovascular disorders can be reduced by delaying the onset of diabetes from IGT, and several supportive findings for this have been obtained. For example, the Da Qing IGT and Diabetes Study carried out in China in 1997 has reported that progression of IGT into Type II diabetes is significantly suppressed by diet and exercise (see Non-patent Document 1). As a case where medication is effective, an α-glucosidase inhibitor, acarbose, which inhibits sugar hydrolases to delay sugar absorption from the small intestine has been reported to suppress the development of Type II diabetes from IGT and further significantly suppress the onset of hypertension (see Non-patent Document 2).

In view of the foregoing, to suppress the onset of diabetes, it is important to control IGT by diet therapy, exercise therapy and medication.

Nevertheless, when people suffer from diabetes, it comes to be necessary to control their blood glucose levels at all times. Diabetes is basically treated by diet therapy and exercise therapy; however, when sufficient effect is not obtained by these therapies, medication must be chosen.

On the mammalian small intestinal epithelium, sodium-dependent glucose transporter 1 (SGLT1) is expressed at a high frequency. It is known that SGLT1 serves depending upon sodium and plays a role in active transport of glucose or galactose in the small intestine. Therefore, if glucose taken from a meal can be suppressed, IGT may be prevented or treated. Based on this concept, pyrazole derivatives inhibiting SGLT1 activity have been reported (see Patent Documents 1 to 6).

Furthermore, sodium-dependent glucose transporter 2 (SGLT2) is expressed at a high frequency in the kidney. Glucose once filtered by the glomeruli is reabsorbed via SGLT2 (see Non-patent Document 3). When an SGLT2 inhibitor is administered to diabetic rats, sugar excretion into urine is facilitated to induce a hypoglycemic action. From this, an SGLT2-specific inhibitor has been considered as a target molecule serving as a novel therapeutic agent for diabetes (see Non-patent Document 4). In these circumstances, studies have been conducted on SGLT2 inhibitors, and various types of O-aryl glycoside derivatives have been provided (see Patent Documents 7 and 8).

Accordingly, if SGLT1 and SGLT2 activities can be inhibited simultaneously, a novel type of therapeutic agent for diabetes can be provided, which has not only postprandial hyperglycemia suppression action ascribed to SGLT1 inhibition but also progressive hypoglycemic action ascribed to SGLT2 inhibition.

Up to now, C-phenyl glucitol derivatives with selective inhibitory activity against SGLT2 have been reported (see Patent Document 9); however, C-phenyl 1-thioglucitol derivatives strongly inhibiting both SGLT1 and SGLT2 have not yet been reported.

Patent Document 1: International Publication No. WO2002/098893
Patent Document 2: International Publication No. WO2004/014932
Patent Document 3: International Publication No. WO2004/018491
Patent Document 4: International Publication No. WO2004/019958
Patent Document 5: International Publication No. WO2005/121161
Patent Document 6: International Publication No. WO2004/050122
Patent Document 7: European Patent Publication No. 0850948
Patent Document 8: International Publication No. WO2001/068660
Patent Document 9: International Publication No. WO2001/027128
Non-patent Document 1: Pan X R, et al. Diabets Care, vol. 20, p. 534, 1997
Non-patent Document 2: J.-L. Chiasson, et al. Lancent, vol. 359, p. 2072, 2002
Non-patent Document 3: E. M. Wright, Am. J. Physiol. Renal. Physiol., vol. 280, p. F10, 2001
Non-patent Document 4: G. Toggenburger, et al. Biochem. Biophys. Acta., vol. 688, p. 557, 1982

DISCLOSURE OF THE INVENTION

Problems to be Solved by the Invention

The present invention aims to provide C-phenyl 1-thioglucitol compounds which prevent diabetes or suppress postprandial hyperglycemia in diabetes through inhibition of SGLT1 activity to suppress absorption of glucose and other sugars. The present invention further aims to provide C-phenyl 1-thioglucitol compounds expected to serve as prophylactic and/or therapeutic agents for diabetes, which have not only a suppressive effect on absorption of glucose and other sugars but also an excretory effect on urinary sugars through inhibition of both SGLT1 and SGLT2 activities.

Means for Solving the Problems

As a result of extensive and intensive efforts made to overcome the problems stated above, the inventors of the present invention have found that C-phenyl 1-thioglucitol compounds having a specific side chain at the end of the aglycon moiety (hereinafter referred to as "the compounds of the present invention") have an excellent inhibitory effect on SGLT1 activity, or alternatively, have an inhibitory effect on both SGLT1 and SGLT2 activities. This finding led to the completion of the present invention.

Namely, the present invention is directed to a C-phenyl 1-thioglucitol compound of the following formula (I) or a pharmaceutically acceptable salt thereof or a hydrate thereof:

[Formula 1]

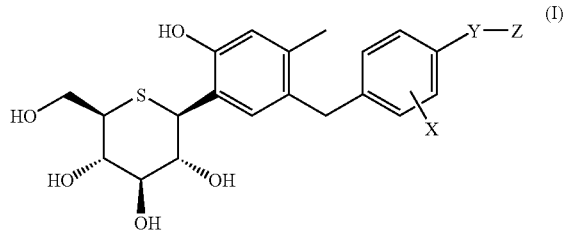

wherein X represents a hydrogen atom or a $C_{1-6}$ alkyl group,

Y represents a $C_{1-6}$ alkylene group or —O—$(CH_2)_n$— (wherein n represents an integer of 1 to 5), and Z represents —$CONHR^A$ or —$NHCONHR^B$ (provided that when Z represents —$NHCONHR^B$, n is not 1), wherein $R^A$ represents a $C_{1-6}$ alkyl group substituted with 1 to 3 substituents selected from the group consisting of a hydroxyl group and —$CONH_2$, and $R^B$ represents a hydrogen atom or a $C_{1-6}$ alkyl group substituted with 1 to 3 substituents selected from the group consisting of a hydroxyl group and —$CONH_2$.

In another embodiment, the present invention is directed to such a C-phenyl 1-thioglucitol compound or a pharmaceutically acceptable salt thereof or a hydrate thereof, wherein Y is a $C_{1-6}$ alkylene group, and $R^B$ is a hydrogen atom or a $C_{1-6}$ alkyl group substituted with a hydroxyl group(s).

In yet another embodiment, the present invention is directed to an inhibitor of sodium-dependent glucose transporter 1 (SGLT1) activity, which comprises the above C-phenyl 1-thioglucitol compound or a pharmaceutically acceptable salt thereof or a hydrate thereof as an active ingredient.

In yet another embodiment, the present invention is directed to an inhibitor of both sodium-dependent glucose transporter 1 (SGLT1) activity and sodium-dependent glucose transporter 2 (SGLT2) activity, which comprises the above C-phenyl 1-thioglucitol compound or a pharmaceutically acceptable salt thereof or a hydrate thereof as an active ingredient.

In yet another embodiment, the present invention is directed to a prophylactic or therapeutic agent for diabetes, which comprises the above C-phenyl 1-thioglucitol compound or a pharmaceutically acceptable salt thereof or a hydrate thereof as an active ingredient.

Advantages of the Invention

The present invention enables the provision of C-phenyl 1-thioglucitol compounds which have an inhibitory effect on SGLT1 activity, or alternatively, which have not only such an inhibitory effect on SGLT1 activity but also an inhibitory effect on SGLT2 activity.

BEST MODE FOR CARRYING OUT THE INVENTION

The terms and phrases used herein are defined as follows.

The term "$C_{1-6}$ alkyl group" is intended to mean a linear or branched alkyl group containing 1 to 6 carbon atoms. Examples include a methyl group, an ethyl group, a n-propyl group, an isopropyl group, a n-butyl group, an isobutyl group, a tert-butyl group, a sec-butyl group, a n-pentyl group and a n-hexyl group.

The term "$C_{1-6}$ alkylene group" is intended to mean a divalent group formed by removing one hydrogen from a carbon atom of a $C_{1-6}$ alkyl group. Examples include a methylene group, an ethylene group, a trimethylene group, a tetramethylene group, a pentamethylene group, a hexamethylene group, a propane-1,2-diyl group and a butane-1,2-diyl group.

The phrase "$C_{1-6}$ alkyl group substituted with 1 to 3 substituents selected from the group consisting of a hydroxyl group and —$CONH_2$" is intended to mean a $C_{1-6}$ alkyl group whose hydrogen atoms are replaced with 1 to 3 substituents selected from at least one of a hydroxyl group and —$CONH_2$. Examples include a hydroxymethyl group, a hydroxyethyl group, a 2-hydroxy-1,1-dimethylethyl group, a 1,3-dihydroxy-2-methylpropan-2-yl group, a 1,3-dihydroxy-2-hydroxymethylpropan-2-yl group, a carbamoylmethyl group and a 2-carbamoylethyl group.

In addition, the term "pharmaceutically acceptable salt" is intended to mean, for example, a salt with an alkali metal, an alkaline earth metal, ammonium or an alkylammonium, or a salt with a mineral acid or an organic acid. Examples include a sodium salt, a potassium salt, a calcium salt, an ammonium salt, an aluminum salt, a triethylammonium salt, an acetate salt, a propionate salt, a butyrate salt, a formate salt, a trifluoroacetate salt, a maleate salt, a tartrate salt, a citrate salt, a stearate salt, a succinate salt, an ethylsuccinate salt, a lactobionate salt, a gluconate salt, a glucoheptate salt, a benzoate salt, a methanesulfonate salt, an ethanesulfonate salt, a 2-hydroxyethanesulfonate salt, a benzenesulfonate salt, a p-toluenesulfonate salt, a lauryl sulfate salt, a malate salt, an aspartate salt, a glutamate salt, an adipate salt, a salt with cysteine, a salt with N-acetylcysteine, a hydrochloride salt, a hydrobromide salt, a phosphate salt, a sulfate salt, a hydroiodide salt, a nicotinate salt, an oxalate salt, a picrate salt, a thiocyanate salt, an undecanoate salt, a salt with an acrylate polymer and a salt with a carboxyvinyl polymer.

The term "hydrate" is intended to mean a pharmaceutically acceptable hydrate of any compound of the present invention or a salt thereof. When exposed to air or recrystallized, the compounds of the present invention or salts thereof may absorb moisture to thereby have adsorbed water or form hydrates. Such hydrates also fall within the scope of the present invention.

Since some compounds and intermediates of the present invention have a chiral center, they may be present in the form of diastereomers or enantiomers. Some compounds and intermediates of the present invention may also be present, for example, as keto-enol tautomers. Moreover, some compounds and intermediates of the present invention may be present as geometrical isomers (E-form, Z-form). Thus, the compounds and intermediates of the present invention encompass all of the above individual isomers and mixtures thereof.

Preferred embodiments will be given below for the compounds of the present invention.

A preferred embodiment of X is a hydrogen atom.

A preferred embodiment of Y is a $C_{1-6}$ alkylene group, and more preferably a $C_{2-4}$ alkylene group.

When Z is —$CONHR^A$, a preferred embodiment of $R^A$ is a $C_{1-4}$ alkyl group substituted with 1 to 3 substituents selected from the group consisting of a hydroxyl group and —$CONH_2$. Likewise, when Z is —$NHCONHR^B$, a preferred embodiment of $R^B$ is a $C_{1-4}$ alkyl group substituted with 1 to 3 hydroxyl groups, and more preferably a $C_{1-4}$ alkyl group substituted with a hydroxyl group.

How to prepare the compound (I) of the present invention will be explained in more detail below by way of some examples, but is not limited to the particular cases illustrated below.

Preparation Procedure 1

The compound (I) of the present invention wherein X is a hydrogen atom or a $C_{1-6}$ alkyl group, Y is a $C_{2-6}$ alkylene group, and Z is —$CONHR^A$ can be synthesized in the following manner.

In the scheme shown below, $Y^1$ represents a single bond or a $C_{1-4}$ alkylene group, $R^1$ and $R^2$, which may be the same or different, each represent a hydrogen atom or a $C_{1-4}$ alkyl group, A represents a chlorine atom or a bromine atom, and the other symbols are as defined above.

thesize compound (IV). Examples of a palladium catalyst used for this purpose include palladium acetate, tetrakis(triphenylphosphine)palladium, dibenzylideneacetone palladium, bis(triphenylphosphine)palladium dichloride, bis(tricyclohexylphosphine)palladium dichloride, and palladium/activated carbon. Examples of a phosphine ligand include triphenylphosphine and tris(2-methylphenyl)phosphine. Likewise, examples of a base available for use include triethylamine, N-ethyl-N,N-diisopropylamine, potassium carbonate, calcium carbonate, cesium carbonate, and potassium t-butoxide. Examples of a solvent available for use in the reaction include acetonitrile, toluene and tetrahydrofuran. The reaction temperature ranges from 0° C. to reflux temperature, or microwave may be used instead.

[Formula 2]

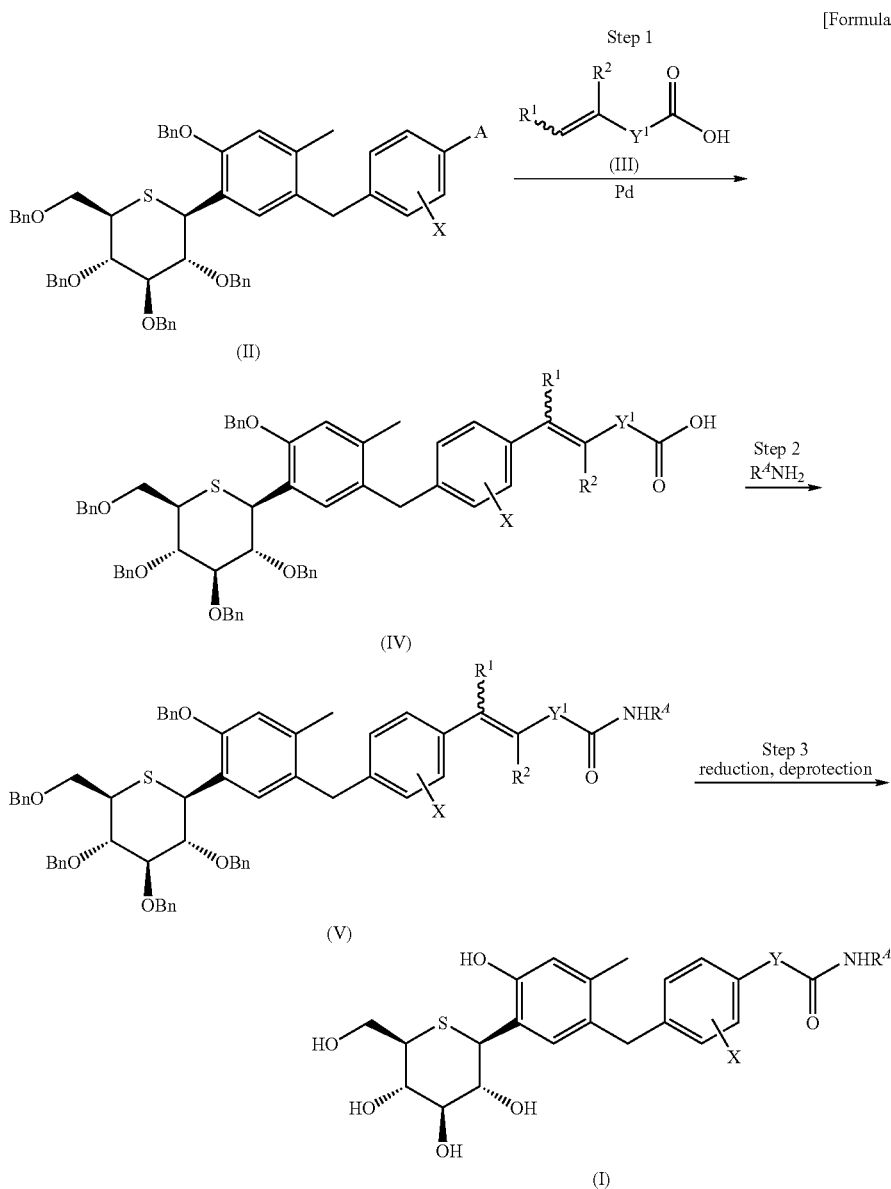

(1) Step 1 (Heck Reaction)

Compound (II) and olefinic carboxylic acid (III) may be subjected to Heck reaction in the presence of a palladium catalyst, a phosphine ligand and an appropriate base to syn- (2) Step 2 (Conversion into Amide)

Compound (IV) may be condensed through dehydration with an amine ($R^A NH_2$) to give compound (V). Examples of a solvent preferred for use in this reaction include chloroform, dichloromethane, and N,N-dimethylformamide. Examples of a dehydration condensing agent preferred for this purpose include N,N'-dicyclohexylcarbodiimide (DCC), N-ethyl-N'-3-dimethylaminopropylcarbodiimide hydrochloride (WSC), 1,1'-carbonyldiimidazole (CDI), and WSC/1-hydroxybenzotriazole monohydrate. The reaction temperature in this case ranges from 0° C. to 60° C.

(3) Step 3 (Reduction and Deprotection)

Compound (V) obtained above may be catalytically hydrogenated using a catalyst (e.g., palladium/activated carbon, palladium hydroxide, or platinum-palladium/activated carbon) under a hydrogen atmosphere to cause olefin reduction and debenzylation at the same time, thereby giving the compound (I) of the present invention. Above all, palladium/activated carbon or palladium hydroxide is preferred as a catalyst. Examples of a solvent available for use in this reaction include methanol, ethanol, isopropanol, ethyl acetate, acetic acid, and mixed solvents thereof. The reaction temperature ranges from room temperature to reflux temperature, with room temperature being preferred.

During debenzylation, it is also possible to use an acid such as $BCl_3$, $BCl_3.Me_2S$, $BBr_3$, $AlCl_3$, $CF_3COOH$ or TfOH. Examples of a solvent available for use in this reaction include chloroform, dichloromethane, acetonitrile, diethyl ether, tetrahydrofuran, dimethyl sulfide, and anisole. Above all, it is preferable to use $CF_3COOH$, TfOH and ethanedithiol in dimethyl sulfide. The reaction temperature desirably ranges from −78° C. to 40° C.

Preparation Procedure 2

The compound (I) of the present invention wherein X is a hydrogen atom or a $C_{1-6}$ alkyl group, Y is a $C_{2-6}$ alkylene group, and Z is —NHCONHR$^B$ can be synthesized in the following manner.

In the scheme shown below, the symbols are as defined above.

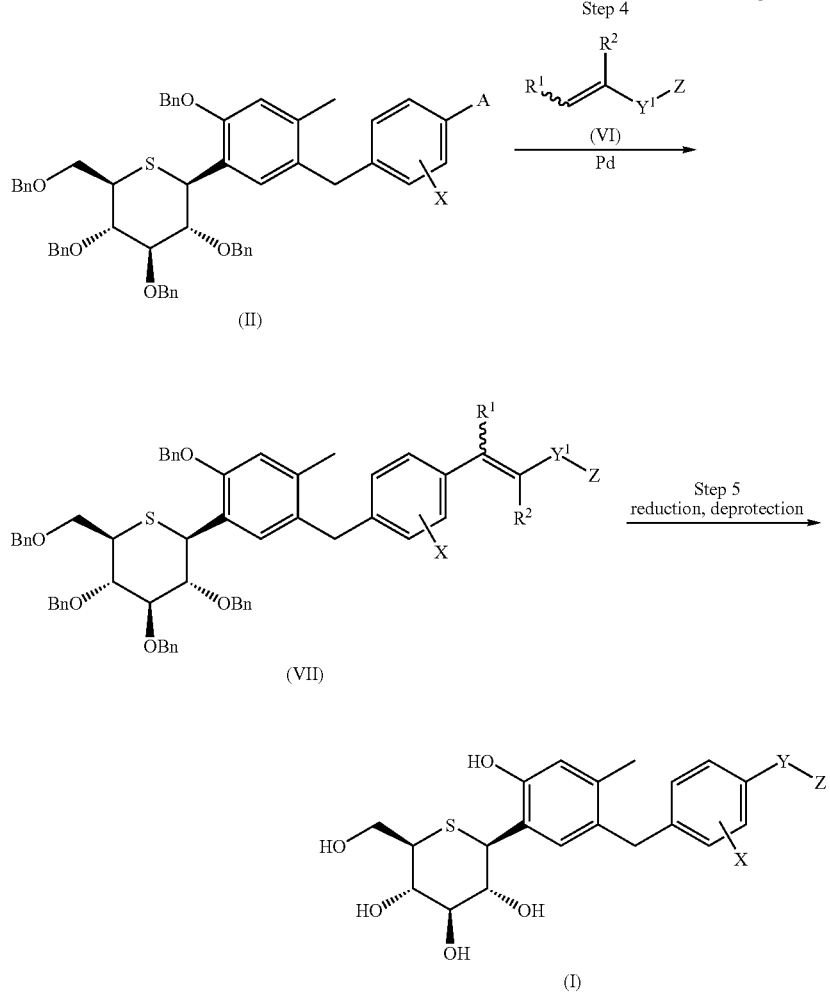

[Formula 3]

(4) Step 4 (Heck Reaction)

Compound (II) and alkenylurea derivative (VI) can be converted into compound (VII) by Heck reaction as shown in Step 1.

(5) Step 5 (Reduction and Deprotection)

Compound (VII) obtained above may be deprotected through catalytic hydrogenation or with a Lewis acid as shown in Step 3 to give the compound (I) of the present invention.

Preparation Procedure 3

The compound (I) of the present invention wherein X is a hydrogen atom or a $C_{1-6}$ alkyl group, Y is —O—$(CH_2)$n-, and Z is —CONHR$^A$ can be synthesized in the following manner.

In the scheme shown below, R³ represents a $C_{1-6}$ alkyl group, and the other symbols are as defined above.

intermediate compound (VIII) may be added to give compound (X). Examples of a solvent available for use in the

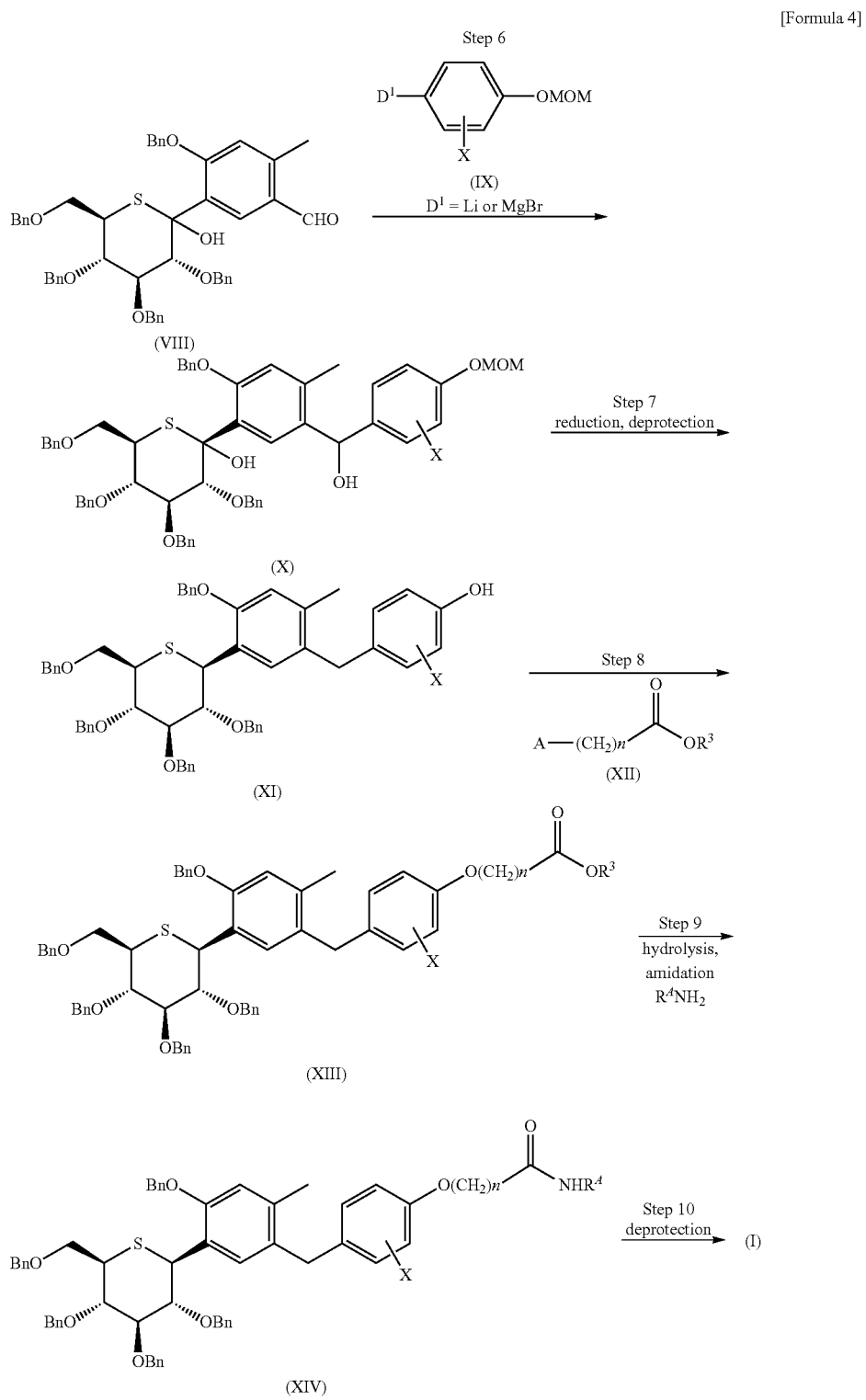

[Formula 4]

(6) Step 6 (Coupling)

An aryl halide may be treated with an organometallic reagent (e.g., n-butyllithium, sec-butyllithium, tert-butyllithium) to prepare aryl lithium reagent (IX). To this reagent, reaction include tetrahydrofuran, diethyl ether, and toluene. The reaction temperature ranges from −80° C. to room temperature, preferably from −78° C. to −25° C. Alternatively, 1 equivalent of metal magnesium may be used to prepare Grignard reagent (IX). Examples of a solvent available for use in the reaction include tetrahydrofuran, diethyl ether, and diglyme.

(7) Step 7 (Reduction and Deprotection)

Compound (X) obtained above and Et$_3$SiH, i-Pr$_3$SiH, t-BuMe$_2$SiH or Ph$_2$SiHCl may be reacted in the presence of a Lewis acid to prepare compound (XI). Examples of a Lewis acid available for use in this reaction include BF$_3$.Et$_2$O, CF$_3$COOH, and InCl$_3$. Examples of a solvent include chloroform, dichloromethane, acetonitrile or mixed solvents thereof, and preferred are mixed solvents with acetonitrile such as acetonitrile-chloroform, acetonitrile-dichloromethane, etc. The reaction temperature in this case ranges from −60° C. to 25° C., preferably from −30° C. to 25° C.

(8) Step 8 (Alkylation)

Compound (XI) and reagent (XII) may be reacted under basic conditions to give compound (XIII). Examples of a base preferred for use in this reaction include sodium carbonate, potassium carbonate, potassium hydroxide, sodium hydride, pyridine, and triethylamine. Examples of a solvent include dioxane, acetonitrile, toluene, dimethoxyethane, tetrahydrofuran, and N,N-dimethylformamide. The reaction temperature preferably ranges from 20° C. to 100° C.

(9) Step 9 (Hydrolysis and Amidation)

Compound (XIII) can be converted into a corresponding carboxylic acid through hydrolysis of the ester moiety under basic conditions. Examples of a base preferred for use in this reaction include potassium carbonate, lithium hydroxide, sodium hydroxide, and triethylamine. Examples of a solvent include methanol, ethanol, ethyl acetate, or mixed solvents thereof with water. The reaction temperature preferably ranges from 20° C. to 100° C.

The carboxylic acid thus obtained can be converted into compound (XIV) through condensation with R$^4$NH$_2$ as shown in Step 2.

(10) Step 10 (Deprotection)

Compound (XIV) can be converted into the titled compound (I) as shown in Step 3.

Preparation Procedure 4

The compound (I) of the present invention wherein X is a hydrogen atom or a C$_{1-6}$ alkyl group, Y is —O—(CH$_2$)n-, and Z is —NHCONHR$^B$ can be synthesized in the following manner.

In the scheme shown below, Y$^2$ represents a C$_{2-5}$ alkylene group, and the other symbols are as defined above.

[Formula 5]

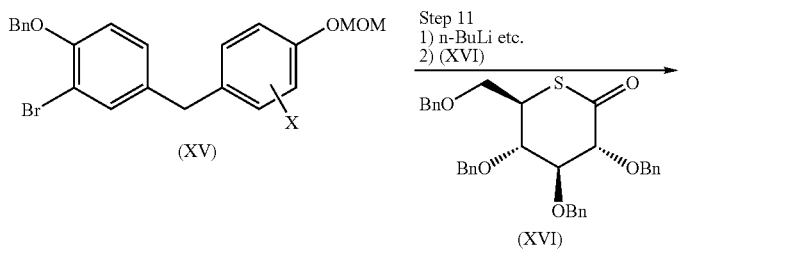

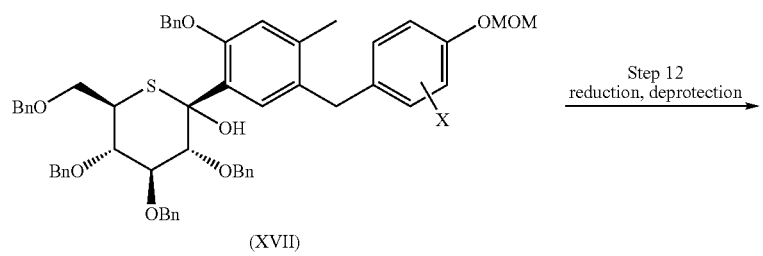

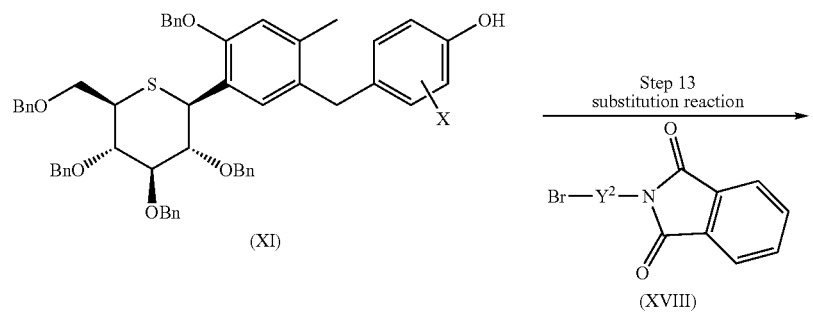

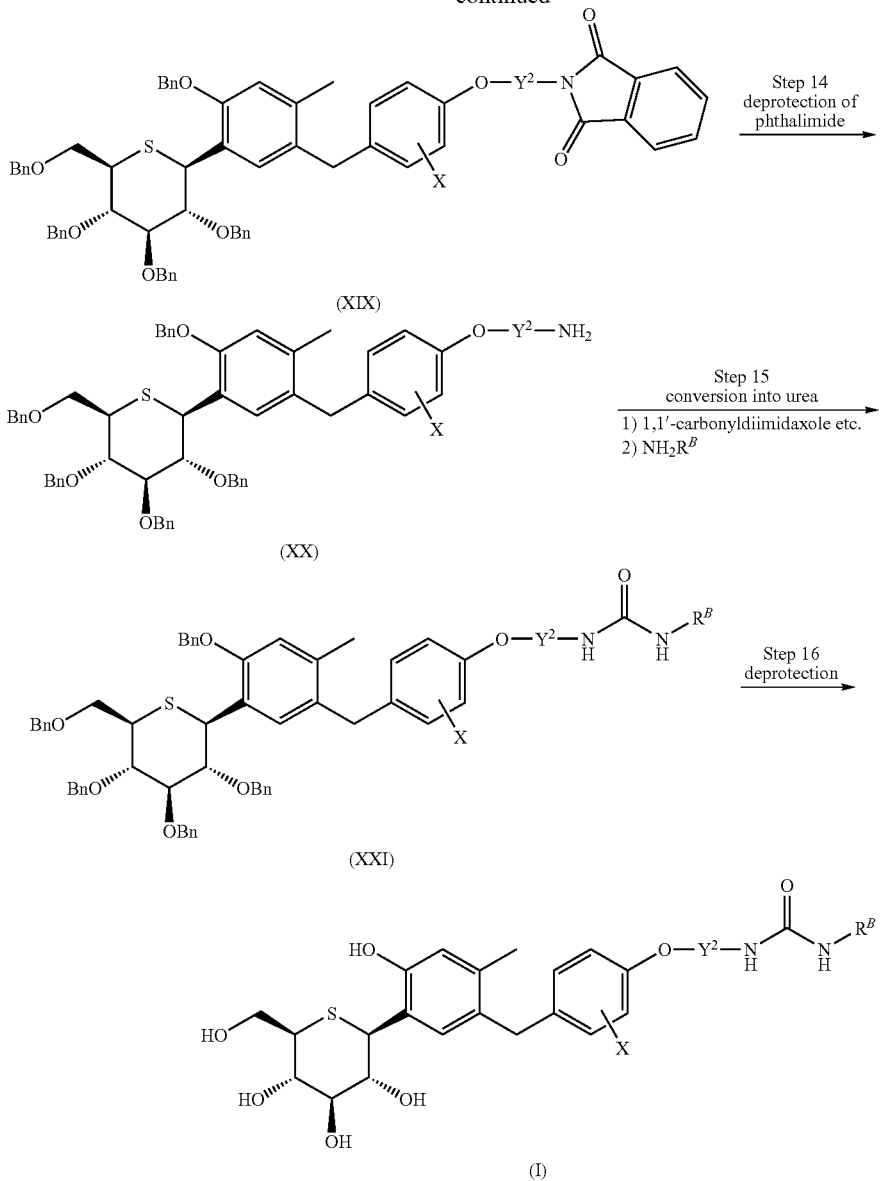

(11) Step 11 (Coupling)

Starting from compound (XV) (which can be prepared according to International Publication No. WO06/073197) and compound (XVI), the same procedure as shown in Step 6 may be repeated to synthesize compound (XVII).

(12) Step 12 (Reduction and Deprotection)

Compound (XVII) may be treated in the same manner as shown in Step 7 to reduce the hydroxyl group and remove the protecting group, thereby synthesizing compound (XI). Compound (XI) may also be synthesized in Step 7 shown above.

(13) Step 13 (Substitution Reaction)

Compound (XI) and reagent (XVIII) may be reacted under basic conditions to give compound (XIX). Examples of a base preferred for use in this reaction include sodium carbonate, potassium carbonate, potassium hydroxide, sodium hydride, pyridine, and triethylamine. Examples of a solvent include dioxane, acetonitrile, toluene, dimethoxyethane, tetrahydrofuran, and N,N-dimethylformamide. The reaction temperature preferably ranges from 20° C. to 100° C.

(14) Step 14 (Deprotection of Phthalimide)

Compound (XIX) and hydrazine hydrate or methyl hydrazine may be reacted in an appropriate solvent to give amine (XX). Examples of a solvent preferred for this purpose include methanol, ethanol, tetrahydrofuran, water, and mixed solvents thereof. The reaction temperature ranges from room temperature to 100° C., preferably from room temperature to 60° C.

(15) Step 15 (Conversion into Urea)

Compound (XX) may be treated with a carbonylating reagent and $NH_2R^B$ to synthesize compound (XXI). Examples of a carbonylating reagent used for this purpose include 1,1'-carbonyldiimidazole, p-nitrophenyl chloroformate, and triphosgene. In this reaction, it is desirable to use a base such as triethylamine, pyridine or N-methylmorpholine. Examples of a solvent used for this purpose include chloroform, dichloromethane, tetrahydrofuran, N,N-dimethylformamide, and dimethyl sulfoxide, or alternatively, mixed solvents thereof may also be used. Preferred mixed solvents are chloroform/N,N-dimethylformamide, chloroform/dimethyl sulfoxide, and tetrahydrofuran/N,N-dimethylformamide. The reaction temperature ranges from room temperature to 80° C. When the reaction proceeds slowly, a higher temperature can be used.

(16) Step 16 (Deprotection)

Compound (XXI) may be deprotected in the same manner as shown in Step 3 to synthesize the titled compound (I).

Preparation Procedure 5

Preparation Procedure for Intermediate (II)

How to prepare intermediates (II) and (VIII) which are required for preparation of the compound (I) of the present invention will be illustrated below. In the following scheme, D¹ represents Li or MgBr, and the other symbols are as defined above.

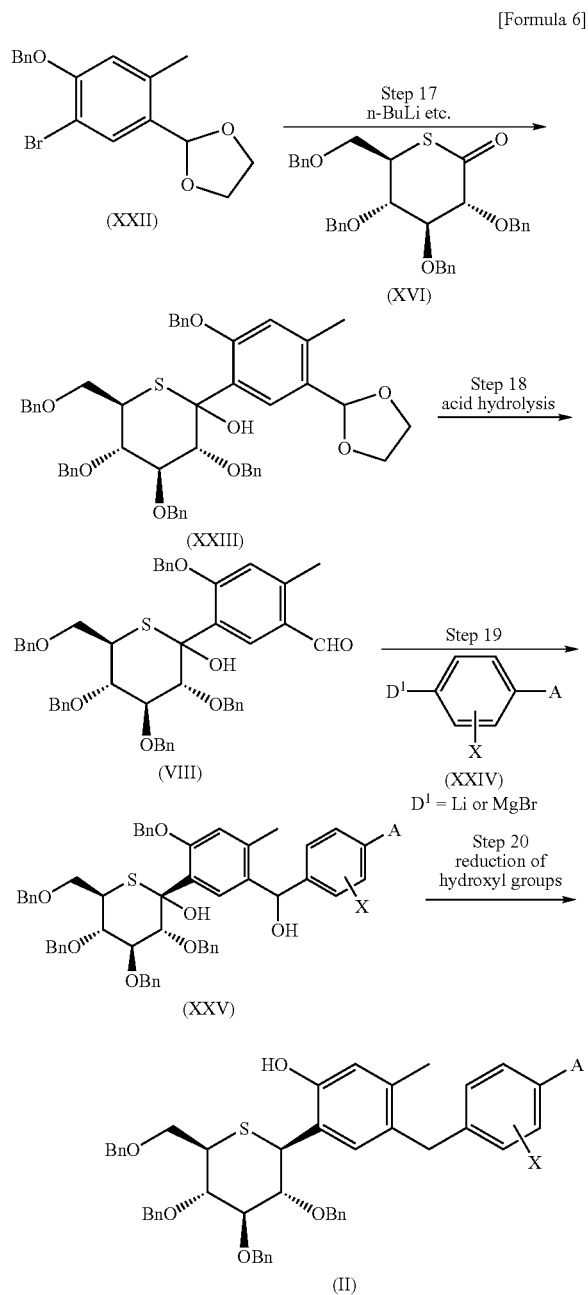

(17) Step 17 (Coupling)

Intermediate compound (XXII) may be treated with an organometallic reagent (e.g., n-butyllithium, sec-butyllithium, tert-butyllithium) to prepare an aryl lithium reagent. To this reagent, thiolactone (XVI) may be added to give compound (XXIII). Examples of a solvent available for use in the reaction include tetrahydrofuran, diethyl ether, and toluene. The reaction temperature ranges from −80° C. to room temperature, preferably from −78° C. to −25° C.

(18) Step 18 (Acid Hydrolysis)

The acetal group in compound (XXIII) may be hydrolyzed with hydrochloric acid, p-toluenesulfonic acid monohydrate or the like to prepare compound (VIII). Examples of a solvent preferred for this purpose include tetrahydrofuran, ethanol, methanol, water, or mixed solvents thereof. The reaction temperature ranges from 4° C. to room temperature, with room temperature being preferred. The reaction time will vary depending on the reaction temperature, but it ranges from 1 to 24 hours.

(19) Step 19 (Coupling)

A 4-halo-bromobenzene derivative may be treated with 1 equivalent of n-butyllithium, sec-butyllithium, tert-butyllithium or the like to prepare monolithium compound (XXIV). Examples of a solvent available for use in the reaction include tetrahydrofuran, diethyl ether, and toluene. The reaction temperature ranges from −80° C. to room temperature, preferably from −78° C. to −25° C. The reaction time preferably ranges from 5 to 30 minutes. Alternatively, 1 equivalent of metal magnesium may be used to prepare Grignard reagent (XXIV). Examples of a solvent available for use in the reaction include tetrahydrofuran, diethyl ether, and diglyme. Next, intermediate compound (VIII) may be added to compound (XXIV) to prepare compound (XXV). The reaction temperature ranges from −80° C. to room temperature, preferably from −78° C. to −25° C.

(20) Step 20 (Reduction of Hydroxyl Groups)

Compound (XXV) obtained above may be reacted under the conditions shown in Step 7 to prepare the titled compound (II).

Preparation Procedure 6

Preparation Procedure for Thiolactone (XVI)

Compound (XVI) can be synthesized as described in Yuasa, H., et al. J. Chem. Soc. Perkin Trans. 1, page 2763, 1990. Alternatively, compound (XVI) can be prepared according to the following scheme.

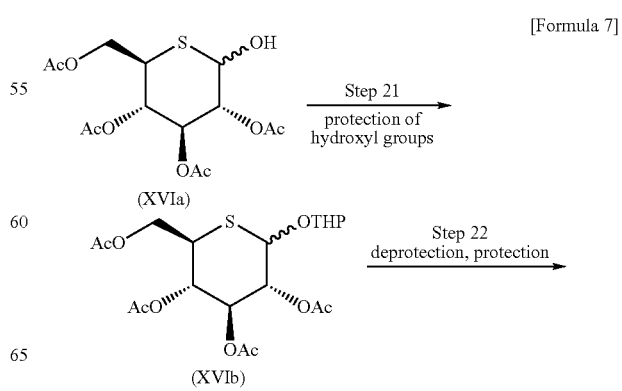

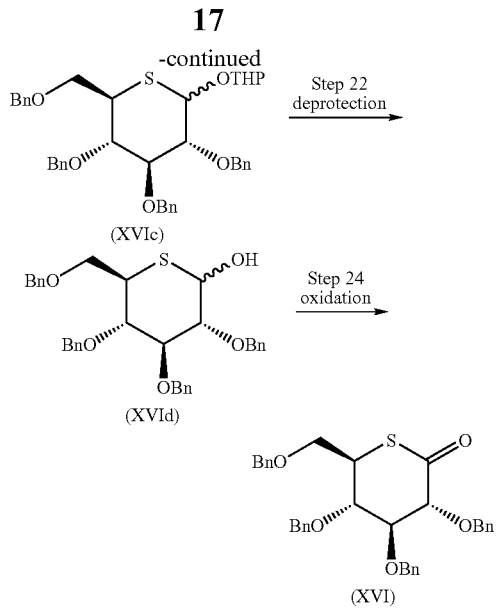

(21) Step 21 (Protection of Hydroxyl Group)

The hydroxyl group at the 1-position of compound (XVIa) (which can be prepared according to International Publication No. WO04/106352) is protected with a protecting group which is resistant to basic conditions and is deprotectable under neutral or acidic conditions. For example, the hydroxyl group is protected with a tetrahydropyranyl group using 3,4-dihydro-2H-pyran (3,4-DHP) and p-toluenesulfonic acid monohydrate or pyridinium-toluenesulfonic acid (PPTS) to synthesize compound (XVIb). Examples of a solvent available for use in this reaction include N,N-dimethylformamide, tetrahydrofuran, dioxane, dimethoxyethane, chloroform, dichloromethane, and toluene.

(22) Step 22 (Deprotection and Protection)

Next, the acetyl groups are removed. For removal of the acetyl groups, a base such as sodium methoxide, sodium hydroxide, lithium hydroxide, potassium carbonate, cesium carbonate or triethylamine may be used, and a solvent such as methanol, ethanol or aqueous methanol may be used. Removal of the acetyl groups may be followed by treatment with benzyl bromide or benzyl chloride using an appropriate base to give compound (XVIc). Examples of a base include triethylamine, N-ethyl-N,N-diisopropylamine, pyridine, potassium carbonate, calcium carbonate, cesium carbonate, sodium hydride, potassium hydride, sodium methoxide and t-BuOK, with potassium carbonate, calcium carbonate, cesium carbonate and sodium hydride being preferred. Examples of a solvent available for use in this reaction include N,N-dimethylformamide, tetrahydrofuran, dioxane, and dimethoxyethane. The reaction temperature ranges from −20° C. to 25° C.

(23) Step 23 (Deprotection)

Next, the protecting group at the 1-position is deprotected to give compound (XVId). For example, compound (XVIc) may be treated in methanol or ethanol with p-toluenesulfonic acid monohydrate or PPTS to remove the THP group.

(24) Step 24 (Oxidation)

In the final step, compound (XVId) may be treated with an appropriate oxidizing agent to prepare thiolactone (XVI). Examples of an oxidizing agent preferred for use in this reaction include dimethyl sulfoxide-acetic anhydride, Dess-Martin periodinane, and IBX. The reaction temperature ranges from 0° C. to 40° C.

The compounds of the present invention inhibit SGLT1 activity to suppress glucose absorption from the digestive tract. Alternatively, the compounds of the present invention inhibit both SGLT1 and SGLT2 activities to improve IGT through not only suppression of glucose absorption but also excretion of urinary sugars, thereby allowing prevention or treatment of diabetes.

Thus, the compounds of the present invention can be used as active ingredients in SGLT1 or SGLT2 inhibitors or in prophylactic or therapeutic agents for diabetes, diabetes-related diseases and diabetic complications.

As used herein, the term "diabetes" encompasses type I diabetes, type II diabetes, and other types of diabetes with specific etiology.

As used herein, the term "diabetes-related diseases" includes obesity, hyperinsulinemia, abnormal carbohydrate metabolism, hyperlipidemia, hypercholesterolemia, hypertriglyceridemia, abnormal lipid metabolism, hypertension, congestive heart failure, edema, hyperuricemia and gout.

As used herein, the term "diabetic complications" can be classified into acute complications and chronic complications.

"Acute complications" include hyperglycemia (e.g., ketoacidosis), infections (e.g., skin, soft tissue, biliary system, respiratory system and urinary tract infections), etc.

"Chronic complications" include microangiopathy (e.g., nephropathy, retinopathy), arteriosclerosis (e.g., atherosclerosis, heart infarction, brain infarction, lower extremity arterial occlusion), neuropathy (e.g., sensory nerves, motor nerves, autonomic nerves), foot gangrene, etc.

Major complications are diabetic retinopathy, diabetic nephropathy and diabetic neuropathy.

With the aim of enhancing their action or reducing their dosage, the compounds of the present invention may also be used in combination with any drug (hereinafter abbreviated as a partner drug) which depends on a different mechanism of action other than inhibition of SGLT1 or SGLT2 activity, such as a therapeutic agent for diabetes, a therapeutic agent for diabetic complications, an antihyperlipidemic agent, a hypotensive agent, an antiobesity agent, a diuretic and/or an antithrombotic agent. In this case, there is no limitation on the timing of administering the compound of the present invention and its partner drug(s). They may be administered to a target, either simultaneously or with a time interval(s). The compound of the present invention and its partner drug(s) may be administered as two separate formulations containing the respective active ingredients or may be administered as a single formulation containing both active ingredients. The dosage of partner drugs may be selected as appropriate on the basis of their clinically used doses. Likewise, the ratio between the compound of the present invention and its partner drug(s) may be selected as appropriate for the target to be administered, the route of administration, the disease or symptom to be treated, the combination of drugs, etc. For example, when the target to be administered is human, partner drug(s) may be used in an amount of 0.01 to 100 parts by mass relative to 1 part by mass of the compound of the present invention.

Examples of a therapeutic agent for diabetes include insulin formulations (e.g., animal insulin formulations extracted from bovine and swine pancreases; human insulin formulations synthesized by genetic engineering techniques using *E. coli* or yeast cells; insulin zinc; protamine insulin zinc; insulin fragments or derivatives (e.g., INS-1), oral insulin formulations), insulin resistance-improving agents (e.g., pioglitazone or a salt thereof (preferably hydrochloride salt), rosiglitazone or a salt thereof (preferably maleate salt), Rivoglitazone (CS- 011) (R-119702), Sipoglitazar (TAK-654), Metaglidasen (MBX-102), Naveglitazar (LY-519818), MX-6054, Balaglitazone (N,N-2344), T-131 (AMG131), PPARγ agonists, PPARγ antagonists, PPARγ/α dual agonists, α-glucosidase inhibitors (e.g., voglibose, acarbose, miglitol, emiglitate), biguanides (e.g., phenformin, metformin, buformin or salts thereof (e.g., hydrochloride salt, fumarate salt, succinate salt)), insulin secretion stimulators (sulfonylureas (e.g., tolbutamide, glibenclamide, gliclazide, chlorpropamide, tolazamide, acetohexamide, glyclopyramide, glimepiride, glipizide, glybuzole), repaglinide, senaglinide, nateglinide, mitiglinide or calcium salt hydrates thereof), GPR40 agonists, GPR40 antagonists, GLP-1 receptor agonists (e.g., GLP-1, GLP-1MR, Liraglutide (N,N-2211), Exenatide (AC-2993) (exendin-4), Exenatide LAR, BIM51077, Aib(8,35) hGLP-1(7,37)NH2, CJC-1131, AVE0010, GSK-716155), amylin agonists (e.g., pramlintide), phosphotyrosine phosphatase inhibitors (e.g., sodium vanadate), dipeptidyl peptidase IV inhibitors (e.g., compounds described in WO02/038541, NVP-DPP-278, PT-100, P32/98, Vildagliptin (LAF-237), P93/01, Sitagliptin (MK-431), Saxagliptin (BMS-477118), SYR-322, MP-513, T-6666, GRC-8200), β3 agonists (e.g., AJ-9677, AZ40140), gluconeogenesis inhibitors (e.g., glycogen phosphorylase inhibitors, glucose-6-phosphatase inhibitors, glucagon antagonists, fructose-1,6-bisphosphatase inhibitors), SGLT (sodium-glucose cotransporter) inhibitors (e.g., compounds described in WO04/014931, WO04/089967 and WO06/073197, T-1095, Sergliflozin (GSK-869682), GSK-189075, KGT-1251, KGT-1681, KGA-2727, BMS-512148, AVE2268, SAR7226), 11β-hydroxysteroid dehydrogenase inhibitors (e.g., compounds described in WO06/051662, BVT-3498, INCB13739), GPR119 agonists (e.g., PSN-632408, APD-668), adiponectin or agonists thereof, IKK inhibitors (e.g., AS-2868), AMPK activators, leptin resistance-improving agents, somatostatin receptor agonists, glucokinase activators (e.g., Ro-28-1675), pancreatic lipase inhibitors (e.g., orlistat, ATL-962), and DGAT-1 inhibitors.

Examples of a therapeutic agent for diabetic complications include aldose reductase inhibitors (e.g., tolrestat, epalrestat, zenarestat, zopolrestat, minalrestat, fidarestat, CT-112), neurotrophic factors and enhancers thereof (e.g., NGF, NT-3, BDNF, neurotrophin production/secretion stimulators), neuranagenesis stimulators (e.g., Y-128), PKC inhibitors (e.g., ruboxistaurin mesylate; LY-333531)), AGE inhibitors (e.g., ALT946, pimagedine, pyratoxathine, N-phenacylthiazolium bromide (ALT766), ALT-711, EXO-226, Pyridorin, pyridoxamine), active oxygen scavengers (e.g., thioctic acid), cerebral vasodilators (e.g., tiapride, mexiletine), somatostatin receptor agonists (e.g., BIM23190), and apoptosis signal-regulating kinase-1 (ASK-1) inhibitors.

Examples of an antihyperlipidemic agent include statin compounds (e.g., pravastatin, simvastatin, lovastatin, atorvastatin, fluvastatin, itavastatin, rosuvastatin, pitavastatin or salts thereof (e.g., sodium salt, calcium salt)), squalene synthase inhibitors (e.g., TAK-475), fibrate compounds (e.g., bezafibrate, clofibrate, simfibrate, clinofibrate), ACAT inhibitors (e.g., Avasimibe, Eflucimibe), anion exchange resins (e.g., cholestyramine), probucol, nicotinic acid drugs (e.g., nicomol, niceritrol), ethyl icosapentate, plant sterols (e.g., soysterol, γ-oryzanol), CETP inhibitors (e.g., Torcetrapib, JTT-705, JTT-302, FM-VP4), and cholesterol absorption inhibitors (e.g., Ezetimibe).

Examples of a hypotensive agent include angiotensin-converting enzyme inhibitors (e.g., captopril, enalapril, delapril), angiotensin II antagonists (e.g., candesartan cilexetil, losartan, eprosartan, valsartan, telmisartan, irbesartan, tasosartan, azilsartan (TAK-536)), calcium antagonists (e.g., manidipine, nifedipine, amlodipine, efonidipine, nicardipine), potassium channel openers (e.g., levcromakalim, L-27152, AL0671, NIP-121), and clonidine.

Examples of an antiobesity agent include central antiobesity agents (e.g., dexfenfluramine, fenfluramine, phentermine, sibutramine, amfepramone, dexamfetamine, mazindol, phenylpropanol amine, clobenzorex; MCH receptor antagonists (e.g., compounds described in WO06/035967, SB-568849; SNAP-7941, T-226296); neuropeptide Y antagonists (e.g., CP-422935); cannabinoid receptor antagonists (e.g., Rimonabant (SR-141716), SR-147778); ghrelin antagonists; 11β-hydroxysteroid dehydrogenase inhibitors (e.g., BVT-3498, INCB13739)), pancreatic lipase inhibitors (e.g., orlistat, ATL-962), DGAT-1 inhibitors, β3 agonists (e.g., AJ-9677, AZ40140), peptidic anorectics (e.g., leptin, CNTF (ciliary neurotrophic factor)), cholecystokinin agonists (e.g., lintitript, FPL-15849), and feeding deterrents (e.g., P-57).

Examples of a diuretic include xanthine derivatives (e.g., theobromine sodium salicylate, theobromine calcium salicylate), thiazide formulations (e.g., ethiazide, cyclopenthiazide, trichlormethiazide, hydrochlorothiazide, hydroflumethiazide, bentylhydrochlorothiazide, penflutizide, polythiazide, methyclothiazide), anti-aldosterone formulations (e.g., spironolactone, triamterene), carbonic anhydrase inhibitors (e.g., acetazolamide), chlorobenzenesulfonamide formulations (e.g., chlorthalidone, mefruside, indapamide), azosemide, isosorbide, ethacrynic acid, piretanide, bumetanide, and furosemide.

Examples of an antithrombotic agent include heparin (e.g., heparin sodium, heparin calcium, dalteparin sodium, AVE-5026), warfarin (e.g., warfarin potassium), antithrombins (e.g., argatroban, Ximelagatran, Dabigatran, Odiparcil, Lepirudin, bivalirudin, Desirudin, ART-123, Idraparinux, SR-123781, AZD-0837, MCC-977, TGN-255, TGN-167, RWJ-58436, LB-30870, MPC-0920, Pegmusirudin, Org-426751), thrombolytic agents (e.g., urokinase, tisokinase, alteplase, nateplase, monteplase, pamiteplase), platelet aggregation inhibitors (e.g., ticlepidine hydrochloride, cilostazol, ethyl icosapentate, beraprost sodium, sarpogrelate hydrochloride), factor Xa inhibitors (e.g., Fondaparinux, BAY-59-7939, DU-176b, YM-150, SR-126517, Apixaban, Razaxaban, LY-517717, MLN-102, Octaparine, Otamixaban, EMD-503982, TC-10, CS-3030, AVE-3247, GSK-813893, KFA-1982), and plasma carboxypeptidase B (also known as activated thrombin-activatable fibrinolysis inhibitor [TAFIa]) inhibitors (e.g., AZD-9684, EF-6265, MN-462).

When the compounds of the present invention are provided in the form of pharmaceutical preparations, various types of dosage forms such as solids and solutions may be selected as appropriate. In this case, a pharmaceutically acceptable carrier(s) may also be incorporated. Examples of such a carrier include commonly used excipients, extenders, binders, disintegrating agents, coating agents, sugar-coating agents, pH adjustors, solubilizers, or aqueous or non-aqueous solvents. The compounds of the present invention and these carriers may be formulated into tablets, pills, capsules, granules, powders, solutions, emulsions, suspensions, injections or other dosage forms.

Also, the compounds of the present invention may be included within, e.g., α-, β- or γ-cyclodextrin or methylated cyclodextrin to improve their solubility.

The dosage of the compounds of the present invention will vary depending on the disease or symptom to be treated, body weight, age, sex, the route of administration, etc. The daily dosage for adults is 0.1 to 1000 mg/kg body weight, preferably 0.1 to 200 mg/kg body weight, and more preferably 0.1 to 10 mg/kg body weight, given as a single dose or in divided doses.

EXAMPLES

The present invention will be further described in more detail by way of the following reference examples, examples and test examples.

Reference Example 1

Preparation of 2,3,4,6-tetra-O-benzyl-5-thio-D-glucono-1,5-lactone (compound (XVI))

[Formula 8]

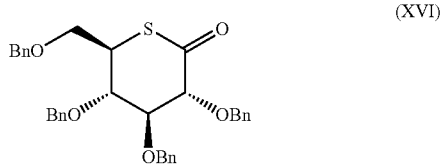

(XVI)

(1) Preparation of tetrahydro-2H-pyran-2-yl 2,3,4,6-tetra-O-acetyl-5-thio-D-glucopyranose To a solution of 2,3,4,6-tetra-O-acetyl-5-thio-D-glucopyranose (2.0 g, 5.49 mmoL) in chloroform (40 mL), 3,4-dihydro-2H-pyran (1.5 mL, 16.5 mmoL) and p-toluenesulfonic acid monohydrate (104 mg, 0.549 mmoL) were added and stirred at room temperature for 1 hour. After addition of saturated aqueous sodium bicarbonate, the reaction mixture was extracted with chloroform, and the organic layer was washed with saturated aqueous sodium chloride and then dried over anhydrous magnesium sulfate. After filtering off the desiccant, the solvent was distilled off under reduced pressure and the resulting residue was purified by silica gel column chromatography (hexane:ethyl acetate=1:1) to give the titled compound (2.56 g) as a light-yellow amorphous substance.

(2) Preparation of tetrahydro-2H-pyran-2-yl 2,3,4,6-tetra-O-benzyl-5-thio-D-glucopyranose Next, to a solution of tetrahydro-2H-pyran-2-yl 2,3,4,6-tetra-O-acetyl-5-thio-D-glucopyranose (2.5 g) in methanol (40 mL), a 25 wt % methanol solution of sodium methoxide (0.11 mL, 0.55 mmoL) was added and stirred for 3 hours. A small amount of dry ice was added to neutralize the reaction mixture, which was then concentrated. The resulting residue was dissolved in N,N-dimethylformamide (20 mL). This solution was added dropwise to a suspension of sodium hydride (1.3 g, 32.9 mmol; 60% in oil) in N,N-dimethylformamide (4 mL) under ice cooling. The reaction mixture was stirred at room temperature for 20 minutes and then cooled to 4° C., followed by addition of benzyl bromide (5.6 g, 32.9 mmoL). The reaction mixture was stirred at room temperature for 12 hours and methanol (5 mL) was added thereto, followed by stirring for 30 minutes. After addition of ice-cold water, the reaction mixture was extracted with ethyl acetate, and the organic layer was washed with saturated aqueous sodium chloride and then dried over anhydrous magnesium sulfate. After filtering off the desiccant, the solvent was distilled off under reduced pressure and the resulting residue was purified by silica gel column chromatography (hexane:ethyl acetate=6:1) to give the titled compound (3.36 g, 96%; 2 steps).

(3) Preparation of 2,3,4,6-tetra-O-benzyl-5-thio-D-glucopyranose

A mixture of tetrahydro-2H-pyran-2-yl 2,3,4,6-tetra-O-benzyl-5-thio-D-glucopyranose (3.30 g, 5.15 mmoL), pyridinium p-toluenesulfonate (518 mg, 2.06 mmoL) and ethanol (58 mL) was stirred at 80° C. for 2 hours. The reaction mixture was cooled to room temperature and the solvent was concentrated. The resulting residue was dissolved in ethyl acetate. This solution was washed with saturated aqueous sodium bicarbonate and saturated aqueous sodium chloride, and then dried over anhydrous magnesium sulfate. After filtering off the desiccant, the residue was purified by silica gel column chromatography (hexane:ethyl acetate=3:1) to give the titled compound (2.89 g, quant.) as a colorless crystal.
$^{13}$C NMR (125 MHz, CHLOROFORM-d) δ 41.3, 67.8, 71.6, 73.0, 73.2, 75.6, 76.2, 81.9, 82.9, 84.4, 127.5, 127.7, 127.8, 127.9, 128.0, 128.3, 128.4, 128.5, 137.8, 138.3, 138.8.

(4) Preparation of 2,3,4,6-tetra-O-benzyl-5-thio-D-glucono-1,5-lactone

A mixture of 2,3,4,6-tetra-O-benzyl-5-thio-D-glucopyranose (2.82 g, 5.07 mmoL), dimethyl sulfoxide (47 mL) and acetic anhydride (39 mL) was stirred at room temperature for 12 hours. After addition of ice-cold water, the reaction mixture was extracted with ethyl acetate. The organic layer was washed with water, saturated aqueous sodium bicarbonate and saturated aqueous sodium chloride, and then dried over anhydrous magnesium sulfate. After filtering off the desiccant, the solvent was distilled off under reduced pressure and the resulting residue was purified by silica gel column chromatography (hexane:ethyl acetate=6:1) to give the titled compound (2.3 g, 82%) as a colorless oil.
$^{1}$H NMR (200 MHz, CHLOROFORM-d) δ ppm 3.70 (d, J=4.8 Hz, 2H) 3.86-4.02 (m, 2H) 4.09-4.22 (m, 2H) 4.40-4.68 (m, 7H) 4.83 (d, J=11.4 Hz, 1H) 7.12-7.41 (m, 20H).

Reference Example 2

Preparation of 2-[4-(benzyloxy)-5-bromo-2-methylphenyl]-1,3-dioxolane (compound (XXII))

[Formula 9]

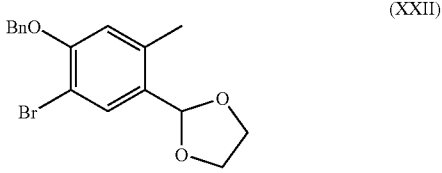

(XXII)

(1) Preparation of 1-[4-(benzyloxy)-2-methylphenyl]ethanone

To a solution of 4'-hydroxy-2'-methylacetophenone (3.06 g, 20 mmol) in N,N-dimethylformamide (20 mL), potassium carbonate (3.66 g, 26.4 mmol), benzyl bromide (2.7 mL, 22.4 mmol) and n-Bu$_4$NI (0.75 g, 2.03 mmol) were added and stirred at room temperature for 14 hours. The reaction mixture was diluted with saturated aqueous ammonium chloride under ice cooling, followed by addition of water and ethyl acetate to separate the organic layer. The organic layer was washed with 20 wt. % aqueous sodium thiosulfate and saturated aqueous sodium chloride, and then dried over anhydrous magnesium sulfate. After filtering off the desiccant, the solvent was distilled off under reduced pressure and the resulting residue was purified by silica gel column chromatography (hexane:ethyl acetate=8:1→6:1) to give the titled compound (5.05 g, quant.) as a colorless powder.

$^1$H NMR (300 MHz, CHLOROFORM-d) δ ppm 2.55 (s, 3H) 2.57 (s, 3H) 5.11 (s, 2H) 6.78-6.86 (m, 2H) 7.30-7.47 (m, 5H) 7.75 (dd, J=7.93, 1.09 Hz, 1H).

(2) Preparation of
4-(benzyloxy)-5-bromo-2-methylbenzoic acid

To a solution of 1-[4-(benzyloxy)-2-methylphenyl]ethanone (20.9 g, 87.1 mmol) in acetone (300 mL), a solution of NaBr (9.86 g, 95.9 mmol) in water (100 mL), water (200 mL) and Oxone® (oxone monopersulfate compound, Aldrich) (59.0 g, 95.9 mmol) were added and stirred at room temperature for 2.5 hours. The reaction mixture was mixed with a solution of sodium sulfite (20 g) in water (50 mL) under ice cooling, followed by addition of water and ethyl acetate to separate the organic layer. The organic layer was washed with 20 wt. % aqueous sodium sulfite and saturated aqueous sodium chloride, and then dried over anhydrous magnesium sulfate. After filtering off the desiccant, the solvent was distilled off under reduced pressure to give a mixture (27.2 g) of 1-[4-(benzyloxy)-5-bromo-2-methylphenyl]ethanone and 1-[4-(benzyloxy)-3-bromo-2-methylphenyl]ethanone. To this mixture, a 5% solution of sodium hypochlorite (300 mL, 255 mmol) and a solution of potassium hydroxide (4.80 g, 85.3 mmol) in water (10 mL) were added and stirred at 120° C. for 1 hour. The reaction mixture was cooled to room temperature and filtered to collect the precipitated insoluble product, to which 2N hydrochloric acid was then added. After extraction with ethyl acetate, the organic layer was washed with 2N hydrochloric acid and saturated aqueous sodium chloride, and then dried over anhydrous magnesium sulfate. After filtering off the desiccant, the solvent was distilled off under reduced pressure and the resulting residue was washed with methanol to give the titled compound (16.6 g, 59%, 2 steps) as a colorless powder.

$^1$H NMR (300 MHz, DMSO-D6) δ ppm 2.45-2.57 (m, 3H) 5.28 (s, 2H) 7.18 (s, 1H) 7.31-7.54 (m, 5H) 8.03 (s, 1H) 12.83 (brs, 1H).

(3) Preparation of 2-[4-(benzyloxy)-5-bromo-2-methylphenyl]-1,3-dioxolane

To a suspension of 4-(benzyloxy)-5-bromo-2-methylbenzoic acid (16.6 g, 51.7 mmol) in chloroform (80 mL), oxalyl chloride (5 mL, 56.9 mmol) and N,N-dimethylformamide (6 drops) were added and stirred at room temperature for 1 hour. The reaction mixture was concentrated to give 4-(benzyloxy)-5-bromo-2-methylbenzoyl chloride. Next, to a suspension of N,O-dimethylhydroxylamine hydrochloride (5.55 g, 56.9 mmol) and triethylamine (15 mL, 103 mmol) in chloroform (60 mL), a solution of 4-(benzyloxy)-5-bromo-2-methylbenzoyl chloride in chloroform (60 mL) was added dropwise under ice cooling and stirred at room temperature for 1 hour, followed by addition of water and chloroform under ice cooling to separate the organic layer. The organic layer was washed with saturated aqueous sodium bicarbonate and saturated aqueous sodium chloride, and then dried over anhydrous magnesium sulfate. After filtering off the desiccant, the solvent was distilled off under reduced pressure to give 4-(benzyloxy)-5-bromo-N-methoxy-N-dimethylbenzamide. To a solution of this product in THF (150 mL), lithium aluminum hydride (1.96 g, 51.7 mmol) was added at −10° C. and stirred at the same temperature for 1 hour. The reaction mixture was diluted with 1N hydrochloric acid, followed by addition of ethyl acetate to separate the organic layer. The organic layer was washed with 1N hydrochloric acid, saturated sodium bicarbonate and saturated aqueous sodium chloride, and then dried over anhydrous magnesium sulfate. After filtering off the desiccant, the solvent was distilled off under reduced pressure to give 4-(benzyloxy)-5-bromo-2-methylbenzaldehyde. To a solution of this product in toluene (120 mL), ethylene glycol (30 mL, 517 mmol) and p-toluenesulfonic acid monohydrate (0.50 g, 2.58 mmol) were added and heated under reflux for 1.5 hours using a Dean-Stark apparatus. Ethyl acetate was added to the reaction mixture to separate the organic layer. The organic layer was washed with water, saturated sodium bicarbonate and saturated aqueous sodium chloride, and then dried over anhydrous magnesium sulfate. After filtering off the desiccant, the solvent was distilled off under reduced pressure, and the resulting residue was purified by silica gel column chromatography (hexane: ethyl acetate=5:1) and further purified by NH-type silica gel column chromatography (chloroform) to give the titled compound (12.8 g, 71%, 3 steps) as a colorless powder.

$^1$H NMR (300 MHz, CHLOROFORM-d) δ ppm 2.34 (s, 3H) 3.92-4.19 (m, 4H) 5.15 (s, 2H) 5.87 (s, 1H) 6.74 (s, 1H) 7.27-7.51 (m, 5H) 7.72 (s, 1H).

ESI m/z=348, 350 (M+2).

Reference Example 3

Preparation of (1S)-1,5-anhydro-2,3,4,6-tetra-O-benzyl-1-[2-(benzyloxy)-5-(4-bromobenzyl)-4-methylphenyl]-1-thio-D-glucitol

[Formula 10]

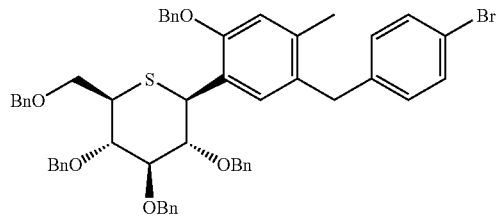

(1) Preparation of 2,3,4,6-tetra-O-benzyl-1-C-[2-(benzyloxy)-5-(1,3-dioxolan-2-yl)-4-methylphenyl]-5-thio-D-glucopyranose To a solution of 2-[4-(benzyloxy)-5-bromo-2-methylphenyl]-1,3-dioxolane (12.9 g, 36.9 mmol) in THF (100 mL), 2.67 M n-butyllithium in hexane (14.5 mL, 36.9 mmol) was added dropwise at −78° C. under a nitrogen atmosphere and stirred at the same temperature for 30 minutes. Then, a solution of 2,3,4,6-tetra-O-benzyl-5-thio-D-glucono-1,5-lactone (9.77 g, 17.6 mmol) in tetrahydrofuran (40 mL) was added dropwise and stirred at the same temperature for 15 minutes. After addition of saturated aqueous ammonium chloride, the reaction mixture was extracted with ethyl acetate. The organic layer was washed with saturated aqueous ammonium chloride and saturated aqueous sodium chloride, and then dried over anhydrous magnesium sulfate. After filtering off the desiccant, the solvent was distilled off under reduced pressure and the resulting residue was purified by silica gel column chromatography (hexane:ethyl acetate=3:1→2:1) to give the titled compound (10.6 g, 73%) as a colorless and transparent amorphous substance.

$^1$H NMR (300 MHz, CHLOROFORM-d) δ ppm 2.39 (s, 3H) 3.46-3.72 (m, 2H) 3.86-4.22 (m, 8H) 4.43-5.00 (m, 8H) 5.10 (s, 2H) 5.92 (s, 1H) 6.66-6.90 (m, 3H) 7.00-7.38 (m, 23H) 7.57 (brs, 1H).

ESI m/z=847 (M+Na).

(2) Preparation of 2,3,4,6-tetra-O-benzyl-1-C-[2-(benzyloxy)-5-formyl-4-methylphenyl]-5-thio-D-glucopyranose To a solution of 2,3,4,6-tetra-O-benzyl-1-C-[2-(benzyloxy)-5-(1,3-dioxolan-2-yl)-4-methylphenyl]-5-thio-D-glucopyranose (11.1 g, 13.5 mmol) in tetrahydrofuran (100 mL), 6N hydrochloric acid (100 mL) was added under ice cooling and stirred at room temperature for 12 hours. After addition of water under ice cooling, the reaction mixture was extracted with ethyl acetate. The organic layer was washed with saturated aqueous sodium bicarbonate and saturated aqueous sodium chloride, and then dried over anhydrous magnesium sulfate. After filtering off the desiccant, the solvent was distilled off under reduced pressure and the resulting residue was purified by silica gel column chromatography (hexane:ethyl acetate=2:1) to give the titled compound (10.1 g, quant.) as a light-yellow oily compound.

$^1$H NMR (300 MHz, CHLOROFORM-d) δ ppm 2.64 (s, 3H) 3.51-3.70 (m, 2H) 3.84-4.29 (m, 4H) 4.46-4.97 (m, 8H) 5.04-5.24 (m, 2H) 6.62-6.82 (m, 3H) 6.99-7.38 (m, 23H) 7.60 (brs, 1H) 10.05 (s, 1H).

ESI m/z=803 (M+Na).

(3) Preparation of (1S)-1,5-anhydro-2,3,4,6-tetra-O-benzyl-1-[2-(benzyloxy)-5-(4-bromobenzyl)-4-methylphenyl]-1-thio-D-glucitol To a solution of 1,4-dibromobenzene (6.08 g, 25.8 mmol) in tetrahydrofuran (50 mL), 2.67 M n-butyllithium in hexane (10.0 mL, 25.8 mmol) was added dropwise at −78° C. under a nitrogen atmosphere. Then, a solution of 2,3,4,6-tetra-O-benzyl-1-C-[2-(benzyloxy)-5-formyl-4-methylphenyl]-5-thio-D-glucopyranose (10.0 g, 13.0 mmol) in tetrahydrofuran (30 mL) was added dropwise and stirred at the same temperature for 15 minutes. After addition of saturated aqueous ammonium chloride, the reaction mixture was extracted with ethyl acetate. The organic layer was washed with saturated aqueous ammonium chloride and saturated aqueous sodium chloride, and then dried over anhydrous magnesium sulfate. After filtering off the desiccant, the solvent was distilled off under reduced pressure and the resulting residue was purified by silica gel column chromatography (hexane:ethyl acetate=3:1→2:1) to give a crude compound (8.89 g) as a yellow amorphous substance.

To a solution of this crude compound (8.89 g) in acetonitrile (60 mL), Et$_3$SiH (4.6 mL, 28.4 mmol) and BF$_3$.Et$_2$O mL, 22.7 mmol) were added at −10° C. under a nitrogen atmosphere and stirred at the same temperature for 20 minutes. The reaction mixture was warmed to room temperature and chloroform (30 mL) was added thereto, followed by stirring for 3.5 hours. After addition of saturated aqueous sodium bicarbonate under ice cooling, the reaction mixture was extracted with chloroform. The organic layer was washed with saturated aqueous sodium bicarbonate and saturated aqueous sodium chloride, and then dried over anhydrous magnesium sulfate. After filtering off the desiccant, the solvent was distilled off under reduced pressure and the resulting residue was purified by silica gel column chromatography (hexane:ethyl acetate=15:1→10:1) to give the titled compound (2.34 g, 20%; 2 steps) as a colorless and transparent amorphous substance.

$^1$H NMR (300 MHz, CHLOROFORM-d) δ ppm 2.14 (s, 3H) 3.05-3.18 (m, 1H) 3.55 (t, J=8.63 Hz, 1H) 3.64-4.10 (m, 7H) 4.48-4.69 (m, 5H) 4.81-5.13 (m, 5H) 6.71-6.95 (m, 4H) 7.03-7.52 (m, 27H).

ESI m/z=922 (M+NH4), 924 (M+2+NH4).

Reference Example 4

Preparation of (1S)-1,5-anhydro-2,3,4,6-tetra-O-benzyl-1-[2-(benzyloxy)-5-(4-chloro-2-methylbenzyl)-4-methylphenyl]-1-thio-D-glucitol

[Formula 11]

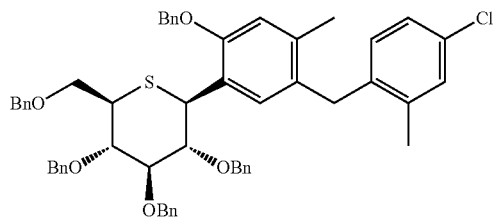

To a solution of 2-bromo-5-chlorotoluene (2.59 g, 12.6 mmol) in tetrahydrofuran (20 mL), 2.64 M n-butyllithium in hexane (4.6 mL, 12.2 mmol) was added dropwise at −78° C. under an argon atmosphere. Then, a solution of 2,3,4,6-tetra-O-benzyl-1-C-[2-(benzyloxy)-5-formyl-4-methylphenyl]-5-thio-D-glucopyranose (3.19 g, 4.08 mmol) in tetrahydrofuran (20 mL) was added dropwise. After addition of water, the reaction mixture was extracted with ethyl acetate and the organic layer was dried over anhydrous magnesium sulfate. After filtering off the desiccant, the solvent was distilled off under reduced pressure and the resulting residue was purified by NH-type silica gel column chromatography (chloroform) to give a crude compound (3.44 g) as a yellow amorphous substance.

To a solution of this crude compound (3.44 g) in acetonitrile-chloroform (1:1, 76 mL), Et$_3$SiH (1.8 mL, 11.4 mmol) and BF$_3$.Et$_2$O (0.53 mL, 4.16 mmol) were added at 0° C. under a nitrogen atmosphere and stirred at room temperature for 2 hours. After addition of saturated aqueous sodium bicarbonate under ice cooling, the reaction mixture was extracted with ethyl acetate and the organic layer was dried over anhydrous magnesium sulfate. After filtering off the desiccant, the solvent was distilled off under reduced pressure and the resulting residue was purified by silica gel column chromatography (hexane:ethyl acetate=10:1) to give the titled compound (1.39 g, 39%) as a colorless and transparent amorphous substance.

$^1$H NMR (300 MHz, CHLOROFORM-d) δ ppm 2.15 (s, 3H) 2.21 (s, 3H) 3.06-3.18 (m, 1H) 3.48-3.61 (m, 1H) 3.62-

3.92 (m, 6H) 3.95-4.07 (m, 1H) 4.45-4.64 (m, 5H) 4.73-4.94 (m, 3H) 5.00-5.14 (m, 2H) 6.52-6.65 (m, 1H) 6.75-6.89 (m, 3H) 6.95-7.50 (m, 26H).

Reference Example 5

Preparation of (1S)-1,5-anhydro-2,3,4,6-tetra-O-benzyl-1-{2-(benzyloxy)-5-[4-((1E)-3-carboxyprop-1-en-1-yl)benzyl]-4-methylphenyl}-1-thio-D-glucitol

[Formula 12]

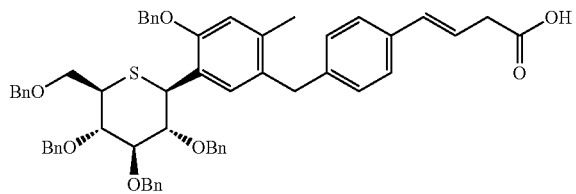

To a solution of (1S)-1,5-anhydro-2,3,4,6-tetra-O-benzyl-1-[2-(benzyloxy)-5-(4-bromobenzyl)-4-methylphenyl]-1-thio-D-glucitol (1.0 g, 1.10 mmol) in acetonitrile (11 mL), vinylacetic acid (227 mg, 2.64 mmol), palladium(II) acetate (49 mg, 0.218 mmol), tri-O-tolylphosphine (135 mg, 0.218 mmol) and triethylamine (558 mg, 5.51 mmol) were added and reacted at 120° C. for 20 minutes using a Biotage microwave system. The reaction mixture was evaporated under reduced pressure and the resulting residue was purified by silica gel column chromatography (hexane:ethyl acetate=5:1→1:1→1:2) to give the titled compound (598 mg, 60%) as an orange-yellow amorphous substance.

$^1$H NMR (300 MHz, CHLOROFORM-d) δ ppm 2.15 (s, 3H) 3.00-3.34 (m, 3H) 3.35-4.18 (m, 8H) 4.45-4.68 (m, 5H) 4.82-4.95 (m, 3H) 4.97-5.16 (m, 2H) 6.00-6.26 (m, 1H) 6.33-6.50 (m, 1H) 6.68-7.51 (m, 31H).

ESI m/z=909 (M−H).

Reference Example 6

Preparation of N-allyl-N'-(2-hydroxy-1,1-dimethylethyl)urea

[Formula 13]

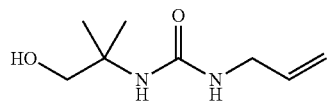

To a solution of allylamine (1.5 g, 26.3 mmol) in chloroform (60 mL), triethylamine (4.9 mL, 35.5 mmol) was added and 4-nitrophenyl chloroformate (6.09 g, 30.2 mmol) was then added at 4° C., followed by stirring for 1 hour. To this reaction mixture, a solution of 2-amino-2-methylpropanol g, 28.9 mmol) in chloroform (3 mL) was added at the same temperature and stirred overnight at room temperature. The reaction solvent was distilled off under reduced pressure and the resulting residue was purified by silica gel column chromatography (hexane:ethyl acetate=1:1→chloroform:methanol=10:1) to give the titled compound g, 24%) as a yellow oily compound.

$^1$H NMR (300 MHz, CHLOROFORM-d) δ ppm 1.26 (s, 6H) 3.55 (s, 2H) 3.71-3.80 (m, 2H) 4.85-5.08 (m, 2H) 5.08-5.24 (m, 2H) 5.77-5.91 (m, 1H).

ESI m/z=195 (M+Na).

Example 1

Preparation of (1S)-1,5-anhydro-1-[2-hydroxy-5-(4-{4-[(2-hydroxy-1,1-dimethylethyl)amino]-4-oxobutyl}benzyl)-4-methylphenyl]-1-thio-D-glucitol

[Formula 14]

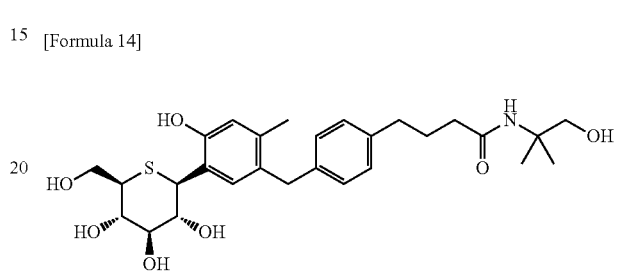

(1) Preparation of (1S)-1,5-anhydro-2,3,4,6-tetra-O-benzyl-1-[2-(benzyloxy)-5-(4-{(1E)-4-[(2-hydroxy-1,1-dimethylethyl)amino]-4-oxobut-1-en-1-yl}benzyl)-4-methylphenyl]-1-thio-D-glucitol To a solution of (1S)-1,5-anhydro-2,3,4,6-tetra-O-benzyl-1-{2-(benzyloxy)-5-[4-((1E)-3-carboxyprop-1-en-1-yl)benzyl]-4-methylphenyl}-1-thio-D-glucitol (410 mg, 0.449 mmol) in chloroform (4.5 mL), 2-amino-2-methyl-1-propanol (100 mg, 1.12 mmol), 1-hydroxybenzotriazole monohydrate (114 mg, 0.846 mmol) and 1-ethyl-3-(3-dimethylaminopropyl)carbodiimide hydrochloride (162 mg, 0.846 mmol) were added and stirred overnight. After addition of water, the reaction mixture was extracted with chloroform. The organic layer was washed with saturated aqueous sodium chloride and then dried over anhydrous magnesium sulfate. After filtering off the desiccant, the solvent was distilled off under reduced pressure and the resulting residue was purified by silica gel column chromatography (hexane:ethyl acetate=1:1→1:2) to give the titled compound (200 mg, 45%) as an orange-yellow oily compound.

$^1$H NMR (300 MHz, CHLOROFORM-d) δ ppm 1.26 (s, 6H) 2.16 (s, 3H) 3.05-3.16 (m, 3H) 3.49-3.61 (m, 3H) 3.64-3.98 (m, 6H) 4.00-4.13 (m, 1H) 4.49-4.65 (m, 5H) 4.81-4.94 (m, 3H) 4.99-5.11 (m, 2H) 5.55-5.62 (m, 1H) 6.04-6.20 (m, 1H) 6.39-6.49 (m, 1H) 6.71-6.83 (m, 3H) 6.92-7.46 (m, 28H).

ESI m/z=1005 (M+Na).

(2) Preparation of (1S)-1,5-anhydro-1-[2-hydroxy-5-(4-{4-[(2-hydroxy-1,1-dimethylethyl)amino]-4-oxobutyl}benzyl)-4-methylphenyl]-1-thio-D-glucitol To a solution of (1S)-1,5-anhydro-2,3,4,6-tetra-O-benzyl-1-[2-(benzyloxy)-5-(4-{(1E)-4-[(2-hydroxy-1,1-dimethylethyl)amino]-4-oxobut-1-en-1-yl}benzyl)-4-methylphenyl]-1-thio-D-glucitol (190 mg, 0.193 mmol) in ethanol (6 mL), palladium hydroxide (200 mg) was added and stirred overnight at room temperature under a hydrogen atmosphere. After the reaction mixture was filtered through celite, the solvent was distilled off under reduced pressure and the resulting residue was purified by silica gel column chromatography (chloroform:methanol=5:1) to give the titled compound (86 mg, 83%) as a colorless powder. NMR and MS data are shown in Table 1-1.

Example 2

Preparation of (1S)-1,5-anhydro-1-{2-hydroxy-5-[4-(4-{[2-hydroxy-1-(hydroxymethyl)-1-methylethyl]amino}-4-oxobutyl)benzyl]-4-methylphenyl}-1-thio-D-glucitol

[Formula 15]

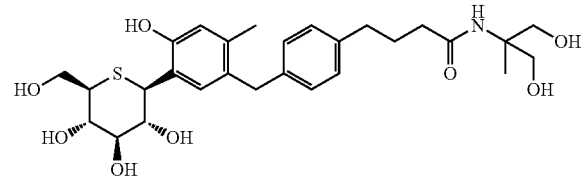

(1) Preparation of (1S)-1,5-anhydro-2,3,4,6-tetra-O-benzyl-1-{2-(benzyloxy)-5-[4-((1E)-4-{[2-hydroxy-1-(hydroxymethyl)-1-methylethyl]amino}-4-oxobut-1-en-1-yl)benzyl]-4-methylphenyl}-1-thio-D-glucitol The same procedure as shown in Example 1(1) was repeated to give the titled compound (310 mg) as a light-yellow amorphous substance, except that 2-amino-2-methyl-1-propanol was replaced with 2-amino-2-methyl-1,3-propanediol.

$^1$H NMR (300 MHz, CHLOROFORM-d) δ ppm 1.18 (s, 3H) 2.17 (s, 3H) 3.06-3.19 (m, 3H) 3.48-4.12 (m, 12H) 4.49-4.64 (m, 5H) 4.81-5.11 (m, 5H) 5.99-6.22 (m, 2H) 6.42-6.52 (m, 1H) 6.72-6.85 (m, 3H) 6.93-7.03 (m, 2H) 7.06-7.44 (m, 26H).

ESI m/z=1021 (M+Na).

(2) Preparation of (1S)-1,5-anhydro-1-{2-hydroxy-5-[4-(4-{[2-hydroxy-1-(hydroxymethyl)-1-methylethyl]amino}-4-oxobutyl)benzyl]-4-methylphenyl}-1-thio-D-glucitol The same procedure as shown in Example 1(2) was repeated to give the titled compound (62 mg, 36%) as a colorless powder, except that (1S)-1,5-anhydro-2,3,4,6-tetra-O-benzyl-1-[2-(benzyloxy)-5-(4-{(1E)-4-[(2-hydroxy-1,1-dimethylethyl)amino]-4-oxobut-1-en-1-yl}benzyl)-4-methylphenyl]-1-thio-D-glucitol was replaced with (1S)-1,5-anhydro-2,3,4,6-tetra-O-benzyl-1-{2-(benzyloxy)-5-[4-((1E)-4-{[2-hydroxy-1-(hydroxymethyl)-1-methylethyl]amino}-4-oxobut-1-en-1-yl)benzyl]-4-methylphenyl}-1-thio-D-glucitol. NMR and MS data are shown in Table 1-1.

Example 3

Preparation of (1S)-1,5-anhydro-1-{2-hydroxy-5-[4-(4-{[2-hydroxy-1,1-bis(hydroxymethyl)ethyl]amino}-4-oxobutyl)benzyl]-4-methylphenyl}-1-thio-D-glucitol

[Formula 16]

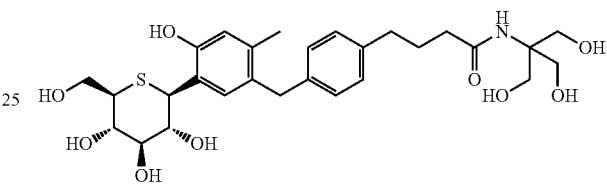

(1) Preparation of (1S)-1,5-anhydro-2,3,4,6-tetra-O-benzyl-1-{2-(benzyloxy)-5-[4-((1E)-4-{[2-hydroxy-1,1-bis(hydroxymethyl)ethyl]amino}-4-oxobut-1-en-1-yl)benzyl]-4-methylphenyl}-1-thio-D-glucitol The same procedure as shown in Example 1(1) was repeated to give the titled compound (290 mg, 70%) as a light-yellow powder, except that 2-amino-2-methyl-1-propanol was replaced with tris(hydroxymethyl)aminomethane.

$^1$H NMR (600 MHz, CHLOROFORM-d) δ ppm 2.19 (s, 3H) 3.06-3.23 (m, 3H) 3.47-4.05 (m, 15H) 4.45-4.69 (m, 5H) 4.79-4.94 (m, 3H) 4.97-5.11 (m, 2H) 6.09-6.23 (m, 1H) 6.48 (d, J=17.88 Hz, 1H) 6.64-6.84 (m, 4H) 6.92-7.02 (m, 2H) 7.09-7.44 (m, 25H).

ESI m/z=1036 (M+Na).

(2) Preparation of (1S)-1,5-anhydro-1-{2-hydroxy-5-[4-(4-{[2-hydroxy-1,1-bis(hydroxymethyl)ethyl]amino}-4-oxobutyl)benzyl]-4-methylphenyl}-1-thio-D-glucitol The same procedure as shown in Example 1(2) was repeated to give the titled compound (45 mg, 28%) as a colorless powder, except that (1S)-1,5-anhydro-2,3,4,6-tetra-O-benzyl-1-[2-(benzyloxy)-5-(4-{(1E)-4-[(2-hydroxy-1,1-dimethylethyl)amino]-4-oxobut-1-en-1-yl}benzyl)-4-methylphenyl]-1-thio-D-glucitol was replaced with (1S)-1,5-anhydro-2,3,4,6-tetra-O-benzyl-1-{2-(benzyloxy)-5-[4-((1E)-4-{[2-hydroxy-1,1-bis(hydroxymethyl)ethyl]amino}-4-oxobut-1-en-1-yl)benzyl]-4-methylphenyl}-1-thio-D-glucitol. NMR and MS data are shown in Table 1-1.

Example 4

Preparation of (1S)-1-[5-(4-{4-[(2-amino-1,1-dimethyl-2-oxoethyl)amino]-4-oxobutyl}benzyl)-2-hydroxy-4-methylphenyl]-1,5-anhydro-1-thio-D-glucitol

[Formula 17]

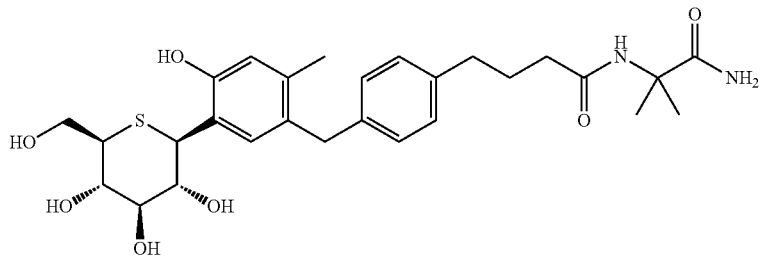

(1) Preparation of (1S)-1-[5-(4-{(1E)-4-[(2-amino-1,1-dimethyl-2-oxoethyl)amino]-4-oxobut-1-en-1-yl}benzyl)-2-(benzyloxy)-4-methylphenyl]-1,5-anhydro-2,3,4,6-tetra-O-benzyl-1-thio-D-glucitol The same procedure as shown in Example 1(1) was repeated to give the titled compound (183 mg, 45%) as a colorless oily compound, except that 2-amino-2-methyl-1-propanol was replaced with 2-amino-2-methylpropionamide.
$^1$H NMR (600 MHz, CHLOROFORM-d) δ ppm 1.57 (s, 6H) 2.15 (s, 3H) 3.12 (d, J=7.34 Hz, 3H) 3.46-4.02 (m, 8H) 4.06 (d, J=11.46 Hz, 1H) 4.46-4.73 (m, 5H) 4.78-4.96 (m, 3H) 4.96-5.13 (m, 2H) 6.04-6.26 (m, 2H) 6.39-6.56 (m, 2H) 6.67-6.85 (m, 3H) 6.90-7.03 (m, 2H) 7.08-7.43 (m, 26H).
ESI m/z=1017 (M+Na).

(2) Preparation of (1S)-1-[5-(4-{4-[(2-amino-1,1-dimethyl-2-oxoethyl)amino]-4-oxobutyl}benzyl)-2-hydroxy-4-methylphenyl]-1,5-anhydro-1-thio-D-glucitol The same procedure as shown in Example 1(2) was repeated to give the titled compound (59 mg, 59%) as a colorless powder, except that (1S)-1,5-anhydro-2,3,4,6-tetra-O-benzyl-1-[2-(benzyloxy)-5-(4-{(1E)-4-[(2-hydroxy-1,1-dimethylethyl)amino]-4-oxobut-1-en-1-yl}benzyl)-4-methylphenyl]-1-thio-D-glucitol was replaced with (1S)-1-[5-(4-{(1E)-4-[(2-amino-1,1-dimethyl-2-oxoethyl)amino]-4-oxobut-1-en-1-yl}benzyl)-2-(benzyloxy)-4-methylphenyl]-1,5-anhydro-2,3,4,6-tetra-O-benzyl-1-thio-D-glucitol. NMR and MS data are shown in Table 1-1.

Example 5

Preparation of (1S)-1,5-anhydro-1-[2-hydroxy-5-(4-{4-[(2-hydroxy-1,1-dimethylethyl)amino]-4-oxobutyl}-2-methylbenzyl)-4-methylphenyl]-1-thio-D-glucitol

[Formula 18]

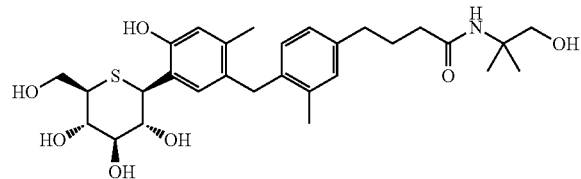

(1) Preparation of (1S)-1,5-anhydro-2,3,4,6-tetra-O-benzyl-1-[2-(benzyloxy)-5-(4-{(1E)-4-[(2-hydroxy-1,1-dimethylethyl)amino]-4-oxobut-1-en-1-yl}-2-methylbenzyl)-4-methylphenyl]-1-thio-D-glucitol To a solution of (1S)-1,5-anhydro-2,3,4,6-tetra-O-benzyl-1-[2-(benzyloxy)-5-(4-chloro-2-methylbenzyl)-4-methylphenyl]-1-thio-D-glucitol (661 mg, 0.755 mmol) in 1,4-dioxane (10 mL), vinylacetic acid (0.15 mL, 1.81 mmol), bis(tricyclohexylphosphine)palladium dichloride (172 mg, 0.233 mmol) and cesium carbonate (836 mg, 2.57 mmol) were added and stirred at 160° C. for 2 hours using a Biotage microwave system. After addition of saturated aqueous ammonium chloride, the reaction mixture was extracted with ethyl acetate and the organic layer was dried over anhydrous magnesium sulfate. After filtering off the desiccant and the palladium catalyst through celite, the solvent was distilled off under reduced pressure. The resulting residue was purified by silica gel column chromatography (hexane:ethyl acetate=4:1) to give a crude compound (577 mg) as a light-yellow amorphous substance.
Further, the crude compound thus obtained (324 mg) was used instead of (1S)-1,5-anhydro-2,3,4,6-tetra-O-benzyl-1-{2-(benzyloxy)-5-[4-((1E)-3-carboxyprop-1-en-1-yl)benzyl]-4-methylphenyl}-1-thio-D-glucitol, and the same procedure as shown in Example 1(1) was repeated to give the titled compound (43 mg, 10%).
$^1$H NMR (300 MHz, CHLOROFORM-d) δ ppm 1.26 (s, 6H) 2.17 (s, 3H) 2.25 (s, 3H) 3.03-3.19 (m, 3H) 3.46-3.65 (m, 3H) 3.63-3.94 (m, 6H) 3.97-4.10 (m, 1H) 4.43-4.71 (m, 5H) 4.74-4.95 (m, 3H) 4.98-5.17 (m, 2H) 5.64-5.73 (m, 1H) 6.04-6.24 (m, 1H) 6.43 (d, J=14.77 Hz, 1H) 6.55-7.54 (m, 30H).

(2) Preparation of (1S)-1,5-anhydro-1-[2-hydroxy-5-(4-{4-[(2-hydroxy-1,1-dimethylethyl)amino]-4-oxobutyl}-2-methylbenzyl)-4-methylphenyl]-1-thio-D-glucitol The same procedure as shown in Example 1(2) was repeated to give the titled compound (22 mg, 93%), except that (1S)-1,5-anhydro-2,3,4,6-tetra-O-benzyl-1-[2-(benzyloxy)-5-(4-{(1E)-4-[(2-hydroxy-1,1-dimethylethyl)amino]-4-oxobut-1-en-1-yl}benzyl)-4-methylphenyl]-1-thio-D-glucitol was replaced with (1S)-1,5-anhydro-2,3,4,6-tetra-O-benzyl-1-[2-(benzyloxy)-5-(4-{(1E)-4-[(2-hydroxy-1,1-dimethylethyl)amino]-4-oxobut-1-en-1-yl}-2-methylbenzyl)-4-methylphenyl]-1-thio-D-glucitol (43 mg). NMR and MS data are shown in Table 1-1.

Example 6

Preparation of (1S)-1-{5-[4-(3-{[(2-hydroxy-1,1-dimethylethyl)aminocarbonyl]amino}propyl)benzyl]-2-hydroxy-4-methylphenyl}-1,5-anhydro-1-thio-D-glucitol

[Formula 19]

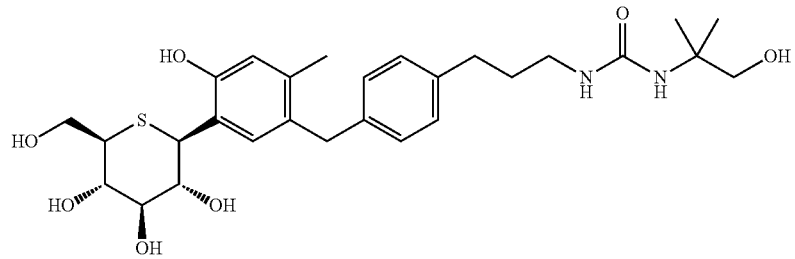

(1) Preparation of (1S)-1-{5-[4-((1E)-3-{[(2-hydroxy-1,1-dimethylethyl)aminocarbonyl]amino}prop-1-en-1-yl)benzyl]-2-(benzyloxy)-4-methylphenyl}-1,5-anhydro-2,3,4,6-tetra-O-benzyl-1-thio-D-glucitol To a solution of (1S)-1,5-anhydro-2,3,4,6-tetra-O-benzyl-1-[2-(benzyloxy)-5-(4-bromobenzyl)-4-methylphenyl]-1-thio-D-glucitol (318 mg, 0.351 mmol) in acetonitrile (3.5 mL), N-allyl-N'-(2-hydroxy-1,1-dimethylethyl)urea (181 mg, 1.05 mmol), palladium(II) acetate (20 mg, 0.0912 mmol), tri-O-tolylphosphine (70 mg, 0.231 mmol) and triethylamine (0.24 mL, 1.75 mmol) were added and stirred at 120° C. for 20 minutes using a Biotage microwave system. After the reaction solvent was distilled off under reduced pressure, the resulting residue was purified by silica gel column chromatography (chloroform→chloroform:methanol=50:1) and further purified by NH-type silica gel column chromatography (chloroform→chloroform:methanol=50:1) to give the titled compound (137 mg, 40%) as a light-yellow amorphous substance.

$^1$H NMR (300 MHz, CHLOROFORM-d) δ ppm 1.21 (s, 6H) 2.14 (s, 3H) 3.06-3.18 (m, 1H) 3.45-3.62 (m, 2H) 3.62-3.99 (m, 8H) 4.01-4.13 (m, 1H) 4.32-4.70 (m, 5H) 4.79-5.17 (m, 6H) 5.52-5.65 (m, 1H) 5.96-6.12 (m, 1H) 6.31-6.43 (m, 1H) 6.70-6.84 (m, 3H) 6.89-7.46 (m, 28H).

ESI m/z=997 (M+H).

(2) Preparation of (1S)-1-{5-[4-(3-{[(2-hydroxy-1,1-dimethylethyl)aminocarbonyl]amino}propyl)benzyl]-2-hydroxy-4-methylphenyl}-1,5-anhydro-1-thio-D-glucitol The same procedure as shown in Example 1(2) was repeated to give the titled compound (20 mg, 30%) as a colorless powder, except that (1S)-1,5-anhydro-2,3,4,6-tetra-O-benzyl-1-[2-(benzyloxy)-5-(4-{(1E)-4-[(2-hydroxy-1,1-dimethylethyl)amino]-4-oxobut-1-en-1-yl}benzyl)-4-methylphenyl]-1-thio-D-glucitol was replaced with (1S)-1-{5-[4-((1E)-3-{[(2-hydroxy-1,1-dimethylethyl)aminocarbonyl]amino}prop-1-en-1-yl)benzyl]-2-(benzyloxy)-4-methylphenyl}-1,5-anhydro-2,3,4,6-tetra-O-benzyl-1-thio-D-glucitol. NMR and MS data are shown in Table 1-1.

Example 7

Preparation of (1S)-1-[5-(4-(3-[(aminocarbonyl)amino]propyl)benzyl)-2-hydroxy-4-methylphenyl]-1,5-anhydro-1-thio-D-glucitol

[Formula 20]

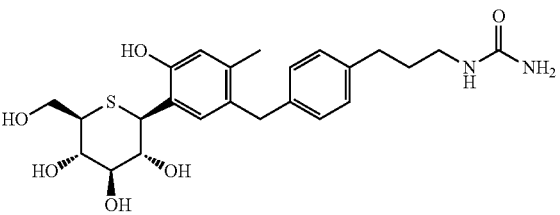

(1) Preparation of (1S)-1-[5-(4-{3-[(aminocarbonyl)amino]propyl}benzyl)-2-(benzyloxy)-4-methylphenyl]-1,5-anhydro-2,3,4,6-tetra-O-benzyl-1-thio-D-glucitol The same procedure as shown in Example 6(1) was repeated to give the titled compound (200 mg, 53%) as a yellow oily compound, except that N-allyl-N'-(2-hydroxy-1,1-dimethylethyl)urea was replaced with allylurea.

$^1$H NMR (300 MHz, CHLOROFORM-d) δ ppm 2.15 (s, 3H) 3.06-3.18 (m, 1H) 3.42-4.13 (m, 10H) 4.32-4.75 (m, 5H) 4.78-5.22 (m, 5H) 5.94-6.12 (m, 1H) 6.39 (d, J=16.16H, 1H) 6.67-6.84 (m, 3H) 6.86-7.46 (m, 28H).

ESI m/z=947 (M+Na).

(2) Preparation of (1S)-1-[5-(4-{3-[(aminocarbonyl)amino]propyl}benzyl)-2-hydroxy-4-methylphenyl]-1,5-anhydro-1-thio-D-glucitol The same procedure as shown in Example 1(2) was repeated to give the titled compound (51 mg, 52%) as a colorless powder, except that (1S)-1,5-anhydro-2,3,4,6-tetra-O-benzyl-1-[2-(benzyloxy)-5-(4-{(1E)-4-[(2-hydroxy-1,1-dimethylethyl)amino]-4-oxobut-1-en-1-yl}benzyl)-4-methylphenyl]-1-thio-D-glucitol was replaced with (1S)-1-[5-(4-{3-[(aminocarbonyl)amino]propyl}benzyl)-2-(benzyloxy)-4-methylphenyl]-1,5-anhydro-2,3,4,6-tetra-O-benzyl-1-thio-D-glucitol. NMR and MS data are shown in Table 1-2.

Example 8

Preparation of (1S)-1,5-anhydro-1-[2-hydroxy-5-(4-{5-[(2-hydroxy-1,1-dimethylethyl)amino]-5-oxopentyl}benzyl)-4-methylphenyl]-1-thio-D-glucitol

[Formula 21]

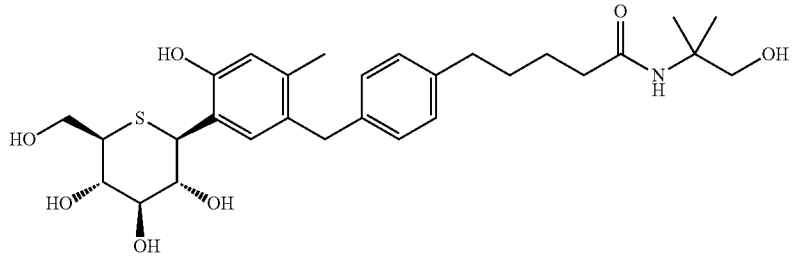

(1) Preparation of (1S)-1,5-anhydro-2,3,4,6-tetra-O-benzyl-1-{2-(benzyloxy)-5-[4-((1E)-4-carboxybut-1-en-1-yl)benzyl]-4-methylphenyl}-1-thio-D-glucitol The same procedure as shown in Reference Example 5 was repeated to give the titled compound (470 mg, 92%) as a brown oil, except that vinylacetic acid was replaced with 4-pentenoic acid.

$^1$H NMR (300 MHz, CHLOROFORM-d) δ ppm 2.20 (s, 3H) 2.33-2.55 (m, 4H) 3.02-5.13 (m, 19H) 5.45-5.93 (m, 2H) 6.70-7.46 (m, 31H).
ESI m/z=923 (M–H).

(2) Preparation of (1S)-1,5-anhydro-2,3,4,6-tetra-O-benzyl-1-[2-(benzyloxy)-5-(4-{(1E)-5-[(2-hydroxy-1,1-dimethylethyl)amino]-5-oxopent-1-en-1-yl}benzyl)-4-methylphenyl]-1-thio-D-glucitol The same procedure as shown in Example 1(1) was repeated to give the titled compound (410 mg, 81%) as a light-brown oil, except that (1S)-1,5-anhydro-2,3,4,6-tetra-O-benzyl-1-{2-(benzyloxy)-5-[4-((1E)-3-carboxyprop-1-en-1-yl)benzyl]-4-methylphenyl}-1-thio-D-glucitol was replaced with (1S)-1,5-anhydro-2,3,4,6-tetra-O-benzyl-1-{2-(benzyloxy)-5-[4-((1E)-4-carboxybut-1-en-1-yl)benzyl]-4-methylphenyl}-1-thio-D-glucitol.

$^1$H NMR (300 MHz, CHLOROFORM-d) δ ppm 1.28 (s, 6H) 2.12-2.54 (m, 7H) 2.85-5.15 (m, 21H) 5.39-5.90 (m, 2H) 6.71-7.47 (m, 31H).
ESI m/z=1018 (M+Na).

(3) Preparation of (1S)-1,5-anhydro-1-[2-hydroxy-5-(4-{5-[(2-hydroxy-1,1-dimethylethyl)amino]-5-oxopentyl}benzyl)-4-methylphenyl]-1-thio-D-glucitol The same procedure as shown in Example 1(2) was repeated to give the titled compound (92 mg, 41%) as a colorless powder, except that (1S)-1,5-anhydro-2,3,4,6-tetra-O-benzyl-1-[2-(benzyloxy)-5-(4-{(1E)-4-[(2-hydroxy-1,1-dimethylethyl)amino]-4-oxobut-1-en-1-yl}benzyl)-4-methylphenyl]-1-thio-D-glucitol was replaced with (1S)-1,5-anhydro-2,3,4,6-tetra-O-benzyl-1-[2-(benzyloxy)-5-(4-{(1E)-5-[(2-hydroxy-1,1-dimethylethyl)amino]-5-oxopent-1-en-1-yl}benzyl)-4-methylphenyl]-1-thio-D-glucitol. NMR and MS data are shown in Table 1-2.

Example 9

Preparation of (1S)-1,5-anhydro-1-[2-hydroxy-5-(4-{3-[(2-hydroxy-1,1-dimethylethyl)amino]-1-methyl-3-oxopropyl}benzyl)-4-methylphenyl]-1-thio-D-glucitol

[Formula 22]

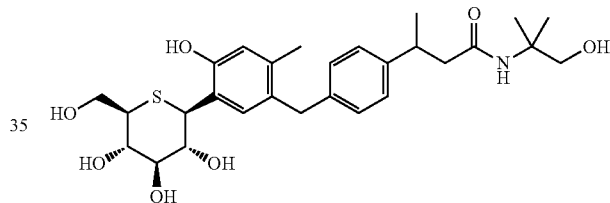

(1) Preparation of (1S)-1,5-anhydro-2,3,4,6-tetra-O-benzyl-1-{2-(benzyloxy)-5-[4-((E)-2-carboxy-1-methylethenyl)benzyl]-4-methylphenyl})-1-thio-D-glucitol The same procedure as shown in Reference Example 5 was repeated to give a crude mixture (280 mg) containing the titled compound, except that vinylacetic acid was replaced with crotonic acid.

$^1$H NMR (300 MHz, CHLOROFORM-d) δ ppm 2.17 (s, 3H) 2.47-2.54 (m, 3H) 3.06-4.11 (m, 11H) 4.44-5.12 (m, 10H) 6.05-6.09 (m, 1H) 6.71-7.46 (m, 31H).
ESI m/z=933 (M+Na).

(2) Preparation of (1S)-1,5-anhydro-2,3,4,6-tetra-O-benzyl-1-[2-(benzyloxy)-5-(4-{(1E)-3-[(2-hydroxy-1,1-dimethylethyl)amino]-1-methyl-3-oxoprop-1-en-1-yl}benzyl)-4-methylphenyl]-1-thio-D-glucitol The same procedure as shown in Example 1(1) was repeated to give the titled compound (120 mg, 15% (2 steps)) as a colorless oil, except that (1S)-1,5-anhydro-2,3,4,6-tetra-O-benzyl-1-{2-(benzyloxy)-5-[4-((1E)-3-carboxyprop-1-en-1-yl)benzyl]-4-methylphenyl}-1-thio-D-glucitol was replaced with (1S)-1,5-anhydro-2,3,4,6-tetra-O-benzyl-1-{2-(benzyloxy)-5-[4-((E)-2-carboxy-1-methylethenyl)benzyl]-4-methylphenyl})-1-thio-D-glucitol.

¹H NMR (300 MHz, CHLOROFORM-d) δ ppm 1.33 (s, 6H) 2.19 (s, 3H) 2.40-2.52 (m, 3H) 3.07-3.17 (m, 1H) 3.48-4.07 (m, 10H) 4.44-4.63 (m, 5H) 4.83-5.10 (m, 5H) 5.48 (brs, 1H) 5.81-5.86 (m, 1H) 6.73-6.81 (m, 3H) 6.97-7.46 (m, 28H). ESI m/z=1004 (M+Na).

(3) Preparation of (1S)-1,5-anhydro-1-(2-hydroxy-5-(4-(3-((2-hydroxy-1,1-dimethylethyl)amino)-1-methyl-3-oxopropyl)benzyl)-4-methylphenyl)-1-thio-D-glucitol The same procedure as shown in Example 1(2) was repeated to give the titled compound (31 mg, 48%) as a colorless powder, except that (1S)-1,5-anhydro-2,3,4,6-tetra-O-benzyl-1-[2-(benzyloxy)-5-(4-{(1E)-4-[(2-hydroxy-1,1-dimethylethyl)amino]-4-oxobut-1-en-1-yl}benzyl)-4-methylphenyl]-1-thio-D-glucitol was replaced with (1S)-1,5-anhydro-2,3,4,6-tetra-O-benzyl-1-[2-(benzyloxy)-5-(4-{(1E)-3-[(2-hydroxy-1,1-dimethylethyl)amino]-1-methyl-3-oxoprop-1-en-1-yl}benzyl)-4-methylphenyl]-1-thio-D-glucitol. NMR and MS data are shown in Table 1-2.

Example 10

Preparation of (1S)-1,5-anhydro-1-[2-hydroxy-5-(4-{3-[(2-hydroxy-1,1-dimethylethyl)amino]-3-oxopropyl}benzyl)-4-methylphenyl]-1-thio-D-glucitol

[Formula 23]

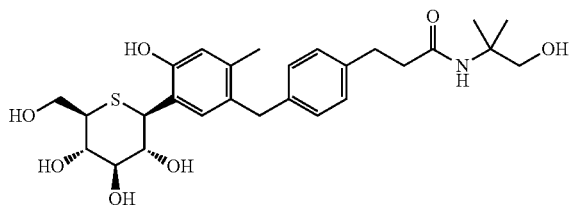

(1) Preparation of (1S)-1,5-anhydro-2,3,4,6-tetra-O-benzyl-1-{2-(benzyloxy)-5-[4-((E)-2-carboxyethenyl)benzyl]-4-methylphenyl}-1-thio-D-glucitol The same procedure as shown in Reference Example 5 was repeated to give the titled compound (365 mg, 74%) as a light-yellow powder, except that vinylacetic acid was replaced with acrylic acid.

¹H NMR (300 MHz, CHLOROFORM-d) δ ppm 2.16 (s, 3H) 3.05-3.19 (m, 1H) 3.47-4.12 (m, 7H) 4.52 (s, 6H) 4.80-5.12 (m, 5H) 6.25-6.38 (m, 1H) 6.73-6.82 (m, 3H) 6.95-7.47 (m, 28H) 7.60-7.73 (m, 1H).

(2) Preparation of (1S)-1,5-anhydro-2,3,4,6-tetra-O-benzyl-1-[2-(benzyloxy)-5-(4-{(1E)-3-[(2-hydroxy-1,1-dimethylethyl)amino]-3-oxoprop-1-en-1-yl}benzyl)-4-methylphenyl]-1-thio-D-glucitol The same procedure as shown in Example 1(1) was repeated to give the titled compound (342 mg, 88%) as a colorless powder, except that (1S)-1,5-anhydro-2,3,4,6-tetra-O-benzyl-1-{2-(benzyloxy)-5-[4-((1E)-3-carboxyprop-1-en-1-yl)benzyl]-4-methylphenyl}-1-thio-D-glucitol was replaced with (1S)-1,5-anhydro-2,3,4,6-tetra-O-benzyl-1-{2-(benzyloxy)-5-[4-((E)-2-carboxyethenyl)benzyl]-4-methylphenyl}-1-thio-D-glucitol.

¹H NMR (300 MHz, CHLOROFORM-d) δ ppm 1.36 (s, 6H) 2.16 (s, 3H) 3.05-3.19 (m, 1H) 3.48-4.09 (m, 10H) 4.34-5.12 (m, 10H) 6.23 (d, J=16.32 Hz, 1H) 6.75 (s, 3H) 6.95-7.59 (m, 29H).

(3) Preparation of (1S)-1,5-anhydro-1-[2-hydroxy-5-(4-{3-[(2-hydroxy-1,1-dimethylethyl)amino]-3-oxopropyl}benzyl)-4-methylphenyl]-1-thio-D-glucitol The same procedure as shown in Example 1(2) was repeated to give the titled compound (84 mg, 46%) as a colorless powder, except that (1S)-1,5-anhydro-2,3,4,6-tetra-O-benzyl-1-[2-(benzyloxy)-5-(4-{(1E)-4-[(2-hydroxy-1,1-dimethylethyl)amino]-4-oxobut-1-en-1-yl}benzyl)-4-methylphenyl]-1-thio-D-glucitol was replaced with (1S)-1,5-anhydro-2,3,4,6-tetra-O-benzyl-1-[2-(benzyloxy)-5-(4-{(1E)-3-[(2-hydroxy-1,1-dimethylethyl)amino]-3-oxoprop-1-en-1-yl}benzyl)-4-methylphenyl]-1-thio-D-glucitol. NMR and MS data are shown in Table 1-2.

Example 11

Preparation of (1S)-1,5-anhydro-1-[2-hydroxy-5-(4-{2-[(2-hydroxy-1,1-dimethylethyl)amino]-2-oxoethoxy}benzyl)-4-methylphenyl]-1-thio-D-glucitol

[Formula 24]

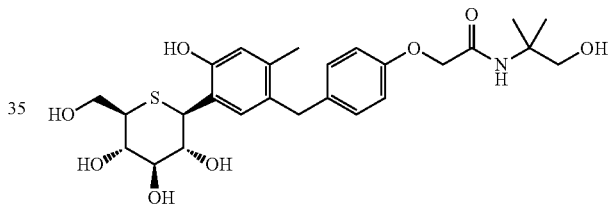

(1) Preparation of 2,3,4,6-tetra-O-benzyl-1-C-[2-(benzyloxy)-5-{hydroxy[4-(methoxymethoxy)phenyl]methyl}-4-methylphenyl]-5-thio-α-D-glucopyranose To a solution of 1-bromo-4-(methoxymethoxy)benzene (1.55 g, 7.13 mmol) in tetrahydrofuran (7.5 mL), 2.67 M n-butyllithium in hexane (2.58 mL, 6.9 mmol) was added dropwise at −60° C. under a nitrogen atmosphere. Then, a solution of 2,3,4,6-tetra-O-benzyl-1-C-[2-(benzyloxy)-5-formyl-4-methylphenyl]-5-thio-D-glucopyranose (1.80 g, 2.30 mmol) in tetrahydrofuran (10 mL) was added dropwise and stirred at −78° C. for 10 minutes. After addition of saturated aqueous ammonium chloride, the reaction mixture was extracted with ethyl acetate. The organic layer was washed with saturated aqueous sodium chloride and dried over anhydrous magnesium sulfate. After filtering off the desiccant, the solvent was distilled off under reduced pressure and the resulting residue was purified by silica gel column chromatography (hexane:ethyl acetate=3:1→1:1) to give the titled compound (1.2 g, 57%) as a yellow amorphous substance.

¹H NMR (300 MHz, CHLOROFORM-d) δ ppm 2.19 (br. s., 3H) 3.46 (s, 7H) 3.89-4.03 (m, 2H) 4.47-4.56 (m, 2H) 4.64 (d, J=11.35 Hz, 1H) 4.73-4.97 (m, 4H) 4.99-5.22 (m, 5H) 5.79-5.95 (m, 1H) 6.66-7.39 (m, 31H).

ESI m/z=942 (M+Na).

(2) Preparation of (1S)-1,5-anhydro-2,3,4,6-tetra-O-benzyl-1-[2-(benzyloxy)-5-(4-hydroxybenzyl)-4-methylphenyl]-1-thio-D-glucitol To an acetonitrile solution of 2,3,4,6-tetra-O-benzyl-1-C—[2-(benzyloxy)-5-{hydroxy[4-(methoxymethoxy)phenyl]methyl}-4-methylphenyl]-5-thio-α-D-glucopyranose obtained above (410 mg), Et₃SiH (0.214 mL, 1.34 mmol) and BF₃.Et₂O (0.062 mL, 0.491 mmol) were added at −15° C. and stirred at the same temperature for 10 minutes. After addition of chloroform, the reaction mixture was warmed to 0° C. and BF₃.Et₂O (0.062 mL, 0.491 mmol) was added thereto, followed by stirring for 30 minutes. After addition of saturated aqueous sodium bicarbonate under ice cooling, the reaction mixture was extracted with chloroform. The organic layer was washed with saturated aqueous sodium chloride and dried over anhydrous magnesium sulfate. After filtering off the desiccant, the solvent was distilled off under reduced pressure and the resulting residue was purified by silica gel column chromatography (hexane:ethyl acetate=4:1) to give the titled compound (0.420 g, 40%) as a colorless oil.

¹H NMR (300 MHz, CHLOROFORM-d) δ ppm 2.17 (s, 3H) 3.06-3.18 (m, 1H) 3.75-3.98 (m, 4H) 4.09-4.15 (m, 1H) 4.43-4.66 (m, 5H) 4.68-4.74 (m, 1H) 4.80-4.95 (m, 3H) 4.98-5.11 (m, 2H) 6.52-7.47 (m, 31H).

(3) Preparation of (1S)-1,5-anhydro-2,3,4,6-tetra-O-benzyl-1-{2-(benzyloxy)-5-[4-(2-methoxy-2-oxoethoxy)benzyl]-4-methylphenyl}-1-thio-D-glucitol To a suspension of (1S)-1,5-anhydro-2,3,4,6-tetra-O-benzyl-1-[2-(benzyloxy)-5-(4-hydroxybenzyl)-4-methylphenyl]-1-thio-D-glucitol obtained above (256 mg, 0.304 mmol) and potassium carbonate (147 mg, 1.06 mmol) in DMF (2.5 mL), methyl bromoacetate (139 mg, 0.912 mmol) and tetrabutylammonium iodide (5 mg) were added and stirred at room temperature for 7 hours. After addition of water, the reaction mixture was extracted with ethyl acetate. The organic layer was washed with saturated aqueous sodium chloride and dried over anhydrous magnesium sulfate. After filtering off the desiccant, the solvent was distilled off under reduced pressure and the resulting residue was purified by silica gel column chromatography (hexane:ethyl acetate=4:1) to give the titled compound (0.230 g, 83%) as a colorless oil.

¹H NMR (300 MHz, CHLOROFORM-d) δ ppm 2.16 (s, 3H) 3.06-3.17 (m, 1H) 3.45-4.13 (m, 10H) 4.34-4.72 (m, 7H) 4.79-4.96 (m, 3H) 4.96-5.11 (m, 2H) 5.19-5.24 (m, 1H) 6.55-7.49 (m, 31H).

ESI m/z=933 (M+NH₄).

(4) Preparation of (1S)-1,5-anhydro-2,3,4,6-tetra-O-benzyl-1-[2-(benzyloxy)-5-(4-{2-[(2-hydroxy-1,1-dimethylethyl)amino]-2-oxoethoxy}benzyl)-4-methylphenyl]-1-thio-D-glucitol To a solution of (1S)-1,5-anhydro-2,3,4,6-tetra-O-benzyl-1-(2-(benzyloxy)-5-[4-(2-methoxy-2-oxoethoxy)benzyl]-4-methylphenyl)-1-thio-D-glucitol synthesized above (210 mg, 0.229 mmol) in THF (1 mL), 2M NaOH was added and stirred at 50° C. for 3 hours. After cooling to 4° C., the reaction mixture was neutralized with 1N HCl and extracted with ethyl acetate. The organic layer was washed with saturated aqueous sodium chloride and dried over anhydrous magnesium sulfate, followed by filtering off the desiccant. The solvent was distilled off under reduced pressure to give a colorless liquid residue (230 mg).

(5) To a solution of the resulting residue in chloroform (2.0 mL), 2-amino-2-methyl-1-propanol (31 mg, 0.344 mmol), 1-hydroxybenzotriazole monohydrate (53 mg, 0.344 mmol) and 1-ethyl-3-(3-dimethylaminopropyl)carbodiimide hydrochloride (66 mg, 0.344 mmol) were added sequentially and stirred for 2 hours. After addition of water, the reaction mixture was extracted with chloroform. The organic layer was washed with saturated aqueous sodium chloride and then dried over anhydrous magnesium sulfate. After filtering off the desiccant, the solvent was distilled off under reduced pressure and the resulting residue was purified by silica gel column chromatography (hexane:ethyl acetate=1:1) to give the titled compound (150 mg, 67%) as a colorless oily compound.

¹H NMR (300 MHz, CHLOROFORM-d) δ ppm 1.31 (s, 6H) 2.17 (s, 3H) 3.07-3.16 (m, 1H) 3.49-3.63 (m, 3H) 3.64-4.09 (m, 7H) 4.25-4.69 (m, 7H) 4.84 (s, 2H) 4.91 (d, J=10.72 Hz, 1H) 5.01-5.11 (m, 2H) 6.51-6.82 (m, 5H) 6.90-7.46 (m, 26H).

ESI m/z=945 (M+Na).

(6) Preparation of (1S)-1,5-anhydro-1-[2-hydroxy-5-(4-{2-[(2-hydroxy-1,1-dimethylethyl)amino]-2-oxoethoxy}benzyl)-4-methylphenyl]-1-thio-D-glucitol The same procedure as shown in Example 1(2) was repeated to give the titled compound (40 mg, 50%) as a colorless powder, except that (1S)-1,5-anhydro-2,3,4,6-tetra-O-benzyl-1-[2-(benzyloxy)-5-(4-{(1E)-4-[(2-hydroxy-1,1-dimethylethyl)amino]-4-oxobut-1-en-1-yl}benzyl)-4-methylphenyl]-1-thio-D-glucitol was replaced with (1S)-1,5-anhydro-2,3,4,6-tetra-O-benzyl-1-[2-(benzyloxy)-5-(4-{2-[(2-hydroxy-1,1-dimethylethyl)amino]-2-oxoethoxy}benzyl)-4-methylphenyl]-1-thio-D-glucitol. NMR and MS data are shown in Table 1-2.

TABLE 1-1

| Example | Structural formula | NMR, MS |
|---|---|---|
| 1 | (structure) | 1H NMR (600 MHz, METHANOL-d4) δ ppm 1.25(s, 6 H) 1.82-1.89(m, 2 H) 2.08(s, 3 H) 2.13-2.17(m, 2 H) 2.57(t, J = 7.57 Hz, 2 H) 2.96-3.02(m, 1 H) 3.26(t, J = 8.71 Hz, 1 H) 3.54-3.62 (m, 3 H) 3.73(dd, J = 11.46, 6.42 Hz, 1 H) 3.81-3.86(m, 3 H) 3.94(dd, J = 11.46, 3.67 Hz, 1 H) 4.30(d, J = 10.55 Hz, 1 H) 6.60(s, 1 H) 6.99-7.03 (m, 2 H) 7.04-7.08(m, 3 H). ESI m/z = 556 (M + Na). |

TABLE 1-1-continued

| Example | Structural formula | NMR, MS |
|---|---|---|
| 2 | | 1H NMR (600 MHz, METHANOL-d4) δ ppm 1.22(s, 3 H) 1.83-1.90(m, 2 H) 2.08(s, 3 H) 2.17-2.21(m, 2 H) 2.58(t, J = 7.79 Hz, 2 H) 2.96-3.01(m, 1 H) 3.26(t, J = 8.94 Hz, 1 H) 3.56-3.67 (m, 5 H) 3.73(dd, J = 11.46, 6.42 Hz, 1 H) 3.81-3.85(m, 3 H) 3.94(dd, J = 11.46, 3.67 Hz, 1 H) 4.29(d, J = 10.55 Hz, 1 H) 6.61(s, 1 H) 6.99-7.03 (m, 2 H) 7.03-7.10(m, 3 H). ESI m/z = 548 (M − H). |
| 3 | | 1H NMR (600 MHz, METHANOL-d4) δ ppm 1.84-1.93(m, 2 H) 2.08(s, 3 H) 2.21-2.27(m, 2 H) 2.60(t, J = 7.57 Hz, 2 H) 2.95-3.01(m, 1 H) 3.26(t, J = 8.71 Hz, 1 H) 3.55-3.61(m, 2 H) 3.69-3.76(m, 6 H) 3.79-3.87(m, 3 H) 3.94(dd, J = 11.46, 3.67 Hz, 1 H) 4.29(d, J = 10.55 Hz, 1 H) 6.60(s, 1 H) 6.99-7.10(m, 5 H). ESI m/z = 588 (M + Na). |
| 4 | | 1H NMR (600 MHz, METHANOL-d4) δ ppm 1.44(s, 6 H) 1.82-1.92(m, 2 H) 2.08(s, 3 H) 2.15-2.22(m, 2 H) 2.58(t, J = 7.79 Hz, 2 H) 2.95-3.02(m, 1 H) 3.26(t, J = 8.94 Hz, 1 H) 3.56-3.60 (m, 1 H) 3.74(dd, J = 11.46, 6.42 Hz, 1 H) 3.79-3.87(m, 3 H) 3.94(dd, J = 11.46, 6.42 Hz, 1 H) 4.29(d, J = 10.55 Hz, 1 H) 6.60(s, 1 H) 6.99-7.09 (m, 5 H). ESI m/z = 569 (M + Na). |
| 5 | | 1H NMR (300 MHz, METHANOL-d4) δ ppm 1.26(s, 6 H) 1.80-1.94(m, 2 H) 2.10(s, 3 H) 2.12-2.20(m, 2 H) 2.24(s, 3 H) 2.50-2.60(m, 2 H) 2.91-3.01(m, 1 H) 3.23(t, J = 8.94 Hz, 1 H) 3.48-3.60(m, 3 H) 3.62-3.81(m, 4 H) 3.92(dd, J = 11.35, 3.73 Hz, 1 H) 4.26(d, J = 10.41 Hz, 1 H) 6.64(s, 1 H) 6.73(d, J = 7.77 Hz, 1 H) 6.83-6.91 (m, 2 H) 6.98(s, 1 H). ESI m/z = 570 (M + Na). |
| 6 | | 1H NMR (600 MHz, METHANOL-d4) δ ppm 1.23(s, 6 H) 1.65-1.77(m, 2 H) 2.07(s ,3 H) 2.57(t, J = 7.79 Hz, 2 H) 2.95-3.02(m, 1 H) 3.05 (t, J = 7.11 Hz, 2 H) 3.25-3.28(m, 1 H) 3.51(s, 2 H) 3.55-3.64(m, 1 H) 3.74(dd, J = 11.69, 6.42 Hz, 1 H) 3.79-3.88(m, 3 H) 3.94(dd, J = 11.69, 3.90 Hz, 1 H) 4.30(d, J = 10.55 Hz, 1 H) 6.60(s, 1 H) 6.96-7.12(m, 5 H). ESI m/z = 549 (M + H). |

TABLE 1-2

| Example | Structural formula | NMR, MS |
|---|---|---|
| 7 | | 1H NMR (600 MHz, METHANOL-d4) δ ppm 1.72-1.79(m, 2 H) 2.08(s, 3 H) 2.58(t, J = 7.57 Hz, 2 H) 2.99-3.12(m, 3 H) 3.29-3.33(m, 1 H) 3.62-3.68(m, 1 H) 3.74-3.95(m, 5 H) 4.33(d, J = 10.55 Hz, 1 H) 6.63(s, 1 H) 6.97-7.09(m, 5 H). ESI m/z = 499 (M + Na). |
| 8 | | 1H NMR (600 MHz, METHANOL-d4) δ ppm 1.24(s, 6 H) 1.55-1.62(m, 4 H) 2.07(s, 3 H) 2.13-2.19(m, 2 H) 2.54-2.60(m, 2 H) 2.95-3.02(m, 1 H) 3.26(t, J = 8.94 Hz, 1 H) 3.53-3.61 (m, 3 H) 3.73(dd, J = 11.46, 6.42 Hz, 1 H) 3.81-3.87(m, 3 H) 3.94(dd, J = 11.46, 3.67 Hz, 1 H) 4.29(d, J = 10.55 Hz, 1 H) 6.60(s, 1 H) 6.97-7.02 (m, 2 H) 7.03-7.07(m, 3 H). ESI m/z = 570 (M + Na). |
| 9 | | 1H NMR (600 MHz, METHANOL-d4) δ ppm 1.09, 1.10, 1.13, 1.14(each s, 6 H) 1.24(d, J = 6.88 Hz, 3 H) 2.07(s, 3 H) 2.31-2.40(m, 2 H) 2.96-3.01(m, 1 H) 3.09-3.17(m, 1 H) 3.27(t, J = 8.71 Hz, 1 H) 3.38-3.48(m, 2 H) 3.58(t, J = 9.63 Hz, 1 H) 3.73(dd, J = 11.46, 6.42 Hz, 1 H) 3.81-3.89(m, 3 H) 3.95(dd, J = 11.46, 3.67 Hz, 1 H) 4.29(d, J = 10.55 Hz, 1 H) 6.60(s, 1 H) 7.00-7.05(m, 2 H) 7.07-7.12(m, 3 H). ESI m/z = 556 (M + Na). |
| 10 | | 1H NMR (600 MHz, METHANOL-d4) δ ppm 1.16(s, 6 H) 2.05(s, 3 H) 2.39(d, J = 7.57 Hz, 2 H) 2.80(t, J = 7.57 Hz, 2 H) 2.93-3.00(m, 1 H) 3.24 (t, J = 8.94 Hz, 1 H) 3.48(s, 2 H) 3.56(dd, J = 10.55, 8.94 Hz, 1 H) 3.72(dd, J = 11.46, 6.88Hz, 1 H) 3.79-3.87(m, 3 H) 3.93(dd, J = 11.46, 3.67 Hz, 1 H) 4.27(d, J = 10.55 Hz, 1 H) 6.58(s, 1 H) 6.97-7.01(m, 2 H) 7.03-7.09(m, 3 H). ESI m/z = 542 (M + Na). 520 (M + H). |
| 11 | | 1H NMR (600 MHz, METHANOL-d4) δ ppm 1.26(s, 6 H) 2.01(s, 3 H) 2.90-2.95(m, 1 H) 3.21(t, J = 8.94 Hz, 1 H) 3.50(s, 2 H) 3.52(dd, J = 10.55, 8.94 Hz, 1 H) 3.67(dd, J = 11.46, 6.42 Hz, 1 H) 3.74-3.80(m, 3 H) 3.88(dd, J = 11.46, 3.67 Hz, 1 H) 4.24(d, J = 10.55 Hz, 1 H) 4.33(s, 2 H) 6.55(s, 1 H) 6.79(d, J = 8.71 Hz, 2 H) 6.96-7.01 (m, 3 H). ESI m/z = 544(M + Na), 522(M + H). |

Formulation Example

Preparation Procedure

A drug (any compound of the present invention) is mixed with lactose monohydrate, crystalline cellulose, carboxymethylcellulose calcium and hydroxypropylcellulose, followed by grinding in a mill. The ground mixture is mixed for 1 minute in a stirring granulator and then granulated with water for 4 to 8 minutes. The resulting granular product is dried at 70° C. for 40 minutes. The dry granular powder is sieved through a 500 µm sieve. The sieved dry granular powder and magnesium stearate are mixed using a V-type blender at 30 rpm for 3 minutes. The granules for tabletting thus obtained are pressed and molded in a rotary tabletting machine to prepare tablets with a tablet weight of 200 mg and a tablet diameter of 8 mm (round). The individual ingredients are used in the amounts indicated in Table 2.

TABLE 2

Formula for tablets containing 100 mg drug:
Contents per tablet:

| | |
|---|---|
| Drug | 108.35 mg |
| Lactose monohydrate | 38.65 mg |
| Crystalline cellulose | 22.00 mg |
| Carboxymethylcellulose calcium | 20.00 mg |
| Hydroxypropylcellulose | 10.00 mg |
| Magnesium stearate | 1.00 mg |
| | 200.00 mg |

Test Example 1

(1) Cloning of Human SGLT1 and Human SGLT2 and their Introduction into Expression Vectors A human SGLT1 sequence (NM_000343) was reverse-transcribed and amplified from human small intestine mRNA, and then introduced into pCMV-tag5A (Stratagene). Likewise, a human SGLT2 sequence (NM_003041) was prepared from human kidney mRNA in the same manner and introduced into pcDNA3.1+hygro (Invitrogen). The individual cloned sequences were confirmed to be identical with the sequences reported.

(2) Creation of CHO-k1 Cells Stably Expressing Human SGLT1 and Human SGLT2

The human SGLT1 and human SGLT2 expression vectors were each transfected into CHO-K1 cells using lipofectamine 2000 (Invitrogen). The cells were cultured in the presence of 500 μg/mL geneticin (SGLT1) or hygromycin B (SGLT2) to select resistant strains and specific activity of sugar uptake in the system shown below was used as an indicator to obtain SGLT-expressing cells.

(3) Inhibition Test for Sodium-Dependent Sugar Uptake in Cells

The cells stably expressing human SGLT1 or human SGLT2 were used for an inhibition test of sodium-dependent glucose uptake activity.

Pretreatment buffer (140 mM choline chloride, 2 mM KCl, 1 mM $CaCl_2$, 1 mM $MgCl_2$, 10 mM HEPES/5 mM Tris, pH 7.4) was added in a volume of 200 μL to human SGLT1-expressing cells and 2 mL to human SGLT2-expressing cells, followed by incubation for 20 minutes. The pretreatment buffer was removed and replaced with uptake buffer containing a test compound (1 mM methyl α-D-glucopyranoside (containing [$^{14}C$]methyl α-D-glucopyranoside), 145 mM NaCl, 2 mM KCl, 1 mM $CaCl_2$, 1 mM $MgCl_2$, 10 mM HEPES/5 mM Tris, pH 7.4) in a volume of 75 μL for SGLT1 and 200 μL for SGLT2. Uptake reaction was performed at 37° C. for 30 minutes (SGLT1) or 1 hour (SGLT2). After the reaction, the cells were washed twice with washing buffer (10 mM methyl α-D-glucopyranoside, 140 mM choline chloride, 2 mM KCl, 1 mM $CaCl_2$, 1 mM $MgCl_2$, 10 mM HEPES/5 mM Tris, pH 7.4) in a volume of 200 μL for SGLT1 and 2 mL for SGLT2, and then dissolved in a 0.2 M NaOH solution (75 μL for SGLT1 and 400 μL for SGLT2). A liquid scintillator (Perkin Elmer) was added and mixed well with each sample, followed by measurement of radioactivity using a microBETA for SGLT1 or a liquid scintillation counter for SGLT2 (Beckman Coulter). For the control group, uptake buffer containing no test compound was prepared. Moreover, another uptake buffer containing choline chloride instead of NaCl was also prepared for basal uptake.

For determination of $IC_{50}$ values, test compounds prepared at 6 appropriate concentrations were used and their concentrations required for 50% inhibition of the amount of sugar uptake ($IC_{50}$ values) were calculated relative to the amount of sugar uptake in the control group (100%). The test results obtained are shown in Table 3.

TABLE 3

| Example | human SGLT1 (nM) | human SGLT2 (nM) |
|---|---|---|
| 1 | 11 | 17 |
| 2 | 22 | 21 |
| 3 | 35 | 31 |
| 4 | 47 | 49 |
| 5 | 20 | 99 |
| 6 | 22 | 32 |
| 8 | 79 | 38 |

Test Example 2

Confirmation Test for Hypoglycemic Effect in Streptozotocin-Induced Diabetic Model Rats (1) Preparation of Diabetic Model Rats SD/IGS rats at 7 weeks of age (male, Charles River Laboratories Japan Inc.) were fasted for about 16 hours and then injected with 50 mg/kg streptozotocin (STZ) via the tail vein under ether anesthesia to prepare diabetic model rats. Similarly, another group of SD/IGS rats was injected with 1.25 mmol/L citric acid in physiological saline (1 mL/kg) via the tail vein under ether anesthesia to prepare normal control rats. At one week (8 weeks of age) after injection of STZ or 1.25 mmol/L citric acid in physiological saline, the rats were provided for an oral glucose tolerance test.

(2) Oral Glucose Tolerance Test

After the rats were fasted for about 16 hours, drug groups were each orally administered with a drug (1 mg/kg) suspended in a 0.5% aqueous carboxymethylcellulose (CMC) solution, while the control group was orally administered with a 0.5% aqueous CMC solution alone. At 5 minutes after drug administration, a glucose solution (2 g/kg) was orally administered and blood was collected at 5 points in total: before drug administration (0 hour) and 0.25, 0.5, 1 and 2 hours after oral administration.

Blood was collected from the orbital venous sinus of each rat under ether anesthesia using a heparin-coated blood collection tube, and centrifuged to separate plasma. Plasma glucose concentrations were quantified by measurement with a Glucose CII-Test Wako (Wako Pure Chemical Industries, Ltd., Japan). To determine the intensity of hypoglycemic effect, blood glucose levels measured between 0 and 1 hour in each drug group were analyzed by the trapezoidal method to calculate the area under the blood glucose-time curve (AUC), followed by basal subtraction to obtain a blood glucose increment (ΔAUC). The results are expressed as a decrease in ΔAUC relative to that of the control group and are shown in Table 4.

TABLE 4

| Example | STZ rat-OGTT (2 g/Kg) % inhibition ΔAUC0-1 h (mgh/dL) @1 mg/Kg |
|---|---|
| 1 | 70.4 |
| 2 | 65.4 |
| 3 | 60.8 |
| 4 | 66.5 |
| 6 | 69.2 |

INDUSTRIAL APPLICABILITY

The present invention can be expected to provide a prophylactic or therapeutic agent for diabetes which comprises, as an active ingredient, a C-phenyl 1-thioglucitol compound having a suppressive effect on absorption of glucose and other sugars through inhibition of the activity of SGLT1 (sodium-dependent glucose transporter 1) expressed in the small intestinal epithelium. Moreover, the present invention can be expected to provide a prophylactic or therapeutic agent for diabetes which comprises, as an active ingredient, a C-phenyl 1-thioglucitol compound having not only such an effect based on inhibition of SGLT1 activity, but also an excretory effect on urinary sugars based on inhibition of the activity of SGLT2 (sodium-dependent glucose transporter 2) expressed in the kidney.

The invention claimed is:

1. A C-phenyl 1-thioglucitol compound of the following formula (I) or a pharmaceutically acceptable salt thereof:

[Formula 1]

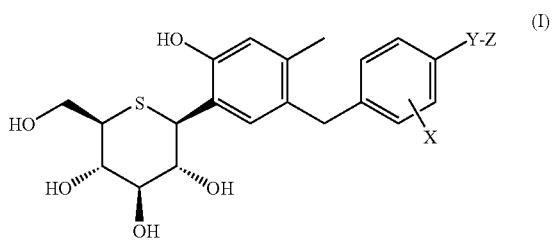

wherein
X represents a hydrogen atom or a $C_{1-6}$ alkyl group,
Y represents a $C_{1-6}$ alkylene, and
Z represents —CONHR$^A$ or —NHCONHR$^B$,
wherein
R$^A$ represents a $C_{1-6}$ alkyl group substituted with 1 to 3 substituents selected from the group consisting of a hydroxyl group and CONH$_2$, and
R$^B$ represents a $C_{1-6}$ alkyl group substituted with a hydroxyl group(s).

* * * * *